US011992418B2

(12) United States Patent
Sharifi-Mehr et al.

(10) Patent No.: US 11,992,418 B2
(45) Date of Patent: *May 28, 2024

(54) EXPANDABLE INTERBODY IMPLANT WITH LATERAL ARTICULATION

(71) Applicant: Howmedica Osteonics Corp., Mahwah, NJ (US)

(72) Inventors: Amir Ali Sharifi-Mehr, Bloomingdale, NJ (US); Oliver Buchert, Franklin Lakes, NJ (US); Ronald Litke, Sandy Hook, CT (US); Thomas A. Alheidt, Sussex, NJ (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 414 days.

This patent is subject to a terminal disclaimer.

(21) Appl. No.: 17/358,735

(22) Filed: Jun. 25, 2021

(65) Prior Publication Data

US 2021/0315712 A1   Oct. 14, 2021

Related U.S. Application Data

(63) Continuation of application No. 16/662,187, filed on Oct. 24, 2019, now Pat. No. 11,071,633, which is a (Continued)

(51) Int. Cl.
*A61F 2/44* (2006.01)
*A61F 2/46* (2006.01)
(Continued)

(52) U.S. Cl.
CPC ............ *A61F 2/4455* (2013.01); *A61F 2/442* (2013.01); *A61F 2/4611* (2013.01);
(Continued)

(58) Field of Classification Search
CPC ........ A61F 2/44; A61F 2/4455; A61F 2/4425; A61F 2002/30537–3054
See application file for complete search history.

(56) References Cited

U.S. PATENT DOCUMENTS 3,875,595 A    4/1975   Froning
4,932,975 A    6/1990   Main et al.
(Continued)

FOREIGN PATENT DOCUMENTS

CN    1756516 A      4/2006
CN    101610741 A   12/2009
(Continued)

OTHER PUBLICATIONS

Extended European Search Report for Application No. 11787340.6 dated Jun. 25, 2014.
(Continued)

*Primary Examiner* — Eduardo C Robert
*Assistant Examiner* — Michelle C Eckman
(74) *Attorney, Agent, or Firm* — Duane Morris LLP

(57) ABSTRACT

An intervertebral implant may include an input for expanding at least two extendable support elements connected to a body at respective locations, such that the extendable support elements each apply a respective expansion force directed away from a surface of the body. Application of a single input force to the input may induce the extendable support elements to apply different amounts of expansion force. Alternatively or additionally, an intervertebral implant may include at least two portions connected together by a hinge for articulation about the hinge. In one aspect, the hinge may include at least two rigid links each pivotably connected to the two portions. In another aspect, a rigid link of the hinge may include a passageway for communicating a hydraulic fluid between the two portions. A locking system
(Continued)

may be positionable into successive locked configurations by operation of a cam to prevent contraction of an extendable support element.

18 Claims, 29 Drawing Sheets

Related U.S. Application Data continuation of application No. 15/794,693, filed on Oct. 26, 2017, now Pat. No. 10,485,675.

(60) Provisional application No. 62/413,038, filed on Oct. 26, 2016.

(51) Int. Cl.
  *A61F 2/30* (2006.01)
  *A61F 2/48* (2006.01)

(52) U.S. Cl.
  CPC .............. *A61F 2002/30329* (2013.01); *A61F 2002/30537* (2013.01); *A61F 2002/30538* (2013.01); *A61F 2002/30556* (2013.01); *A61F 2002/30579* (2013.01); *A61F 2002/4629* (2013.01); *A61F 2/484* (2021.08)

(56) References Cited

U.S. PATENT DOCUMENTS

| | | |
|---|---|---|
| 4,969,888 A | 11/1990 | Scholten et al. |
| 5,236,460 A | 8/1993 | Barber |
| 5,653,763 A | 8/1997 | Errico et al. |
| 5,665,122 A | 9/1997 | Kambin |
| 5,723,013 A | 3/1998 | Jeanson et al. |
| 5,827,328 A | 10/1998 | Buttermann |
| 5,865,848 A | 2/1999 | Baker |
| 5,916,267 A | 6/1999 | Tienboon |
| 5,980,522 A | 11/1999 | Koros et al. |
| 5,989,290 A | 11/1999 | Biedermann et al. |
| 6,039,761 A | 3/2000 | Li et al. |
| 6,102,950 A | 8/2000 | Vaccaro |
| 6,127,597 A | 10/2000 | Beyar et al. |
| 6,176,881 B1 | 1/2001 | Schar et al. |
| 6,176,882 B1 | 1/2001 | Biedermann et al. |
| 6,193,756 B1 | 2/2001 | Studer et al. |
| 6,193,757 B1 | 2/2001 | Foley et al. |
| 6,214,012 B1 | 4/2001 | Karpman et al. |
| 6,296,665 B1 | 10/2001 | Strnad et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,032 B1 | 5/2002 | Gauchet |
| 6,454,806 B1 | 9/2002 | Cohen et al. |
| 6,527,803 B1 | 3/2003 | Crozet et al. |
| 6,562,074 B2 | 5/2003 | Gerbec et al. |
| 6,582,467 B1 | 6/2003 | Teitelbaum et al. |
| 6,585,699 B2 | 7/2003 | Ljunggreen et al. |
| 6,692,495 B1 | 2/2004 | Zacouto |
| 6,719,796 B2 | 4/2004 | Cohen et al. |
| 6,723,126 B1 | 4/2004 | Berry |
| 6,730,088 B2 | 5/2004 | Yeh |
| 6,764,491 B2 | 7/2004 | Frey et al. |
| 6,830,570 B1 | 12/2004 | Frey et al. |
| 6,835,207 B2 | 12/2004 | Zacouto et al. |
| 6,866,682 B1 | 3/2005 | An et al. |
| 6,875,235 B2 | 4/2005 | Ferree |
| 6,953,477 B2 | 10/2005 | Berry |
| 6,960,232 B2 | 11/2005 | Lyons et al. |
| 6,981,989 B1 | 1/2006 | Fleischmann et al. |
| 7,001,431 B2 | 2/2006 | Bao et al. |
| 7,018,415 B1 | 3/2006 | McKay |
| 7,018,416 B2 | 3/2006 | Hanson et al. |
| 7,060,037 B2 | 6/2006 | Lussier et al. |
| 7,060,073 B2 | 6/2006 | Frey et al. |
| 7,066,958 B2 | 6/2006 | Ferree |
| 7,094,257 B2 | 8/2006 | Mujwid et al. |
| 7,166,110 B2 | 1/2007 | Yundt |
| 7,204,853 B2 | 4/2007 | Gordon et al. |
| 7,214,243 B2 | 5/2007 | Taylor |
| 7,217,293 B2 | 5/2007 | Branch, Jr. |
| 7,282,063 B2 | 10/2007 | Cohen et al. |
| 7,291,150 B2 | 11/2007 | Graf |
| 7,291,158 B2 | 11/2007 | Crow et al. |
| 7,316,686 B2 | 1/2008 | Dorchak et al. |
| 7,316,714 B2 | 1/2008 | Gordon et al. |
| 7,351,261 B2 | 4/2008 | Casey |
| 7,407,513 B2 | 8/2008 | Alleyne et al. |
| 7,419,505 B2 | 9/2008 | Fleischmann et al. |
| 7,452,359 B1 | 11/2008 | Michelson |
| 7,470,273 B2 | 12/2008 | Dougherty-Shah |
| 7,481,812 B2 | 1/2009 | Frey et al. |
| 7,485,145 B2 | 2/2009 | Purcell |
| 7,507,241 B2 | 3/2009 | Levy et al. |
| 7,520,900 B2 | 4/2009 | Trieu |
| 7,563,284 B2 | 7/2009 | Coppes et al. |
| 7,563,286 B2 | 7/2009 | Gerber et al. |
| 7,621,956 B2 | 11/2009 | Paul et al. |
| 7,628,815 B2 | 12/2009 | Baumgartner et al. |
| 7,670,359 B2 | 3/2010 | Yundt |
| 7,708,779 B2 | 5/2010 | Edie et al. |
| 7,722,674 B1 | 5/2010 | Grotz |
| 7,731,752 B2 | 6/2010 | Edie et al. |
| 7,731,753 B2 | 6/2010 | Reo et al. |
| 7,771,480 B2 | 8/2010 | Navarro et al. |
| 7,794,501 B2 | 9/2010 | Edie et al. |
| 7,806,935 B2 | 10/2010 | Navarro et al. |
| 7,819,921 B2 | 10/2010 | Grotz |
| 7,824,444 B2 | 11/2010 | Biscup et al. |
| 7,824,445 B2 | 11/2010 | Biro et al. |
| 7,854,766 B2 | 12/2010 | Moskowitz et al. |
| 7,862,618 B2 | 1/2011 | White et al. |
| 7,883,543 B2 | 2/2011 | Sweeney |
| 7,935,124 B2 | 5/2011 | Frey et al. |
| 7,967,863 B2 | 6/2011 | Frey et al. |
| 7,967,867 B2 | 6/2011 | Barreiro et al. |
| 7,985,231 B2 | 7/2011 | Sankaran |
| 7,985,256 B2 | 7/2011 | Grotz et al. |
| 8,021,395 B2 | 9/2011 | Ben-Mokhtar et al. |
| 8,025,680 B2 | 9/2011 | Hayes et al. |
| 8,057,549 B2 | 11/2011 | Butterman et al. |
| 8,062,368 B2 | 11/2011 | Heinz et al. |
| 8,062,373 B2 | 11/2011 | Fabian, Jr. |
| 8,070,813 B2 | 12/2011 | Grotz et al. |
| 8,105,382 B2 | 1/2012 | Olmos et al. |
| 8,153,785 B2 | 4/2012 | Khire et al. |
| 8,187,331 B2 | 5/2012 | Strohkirch, Jr. et al. |
| 8,192,495 B2 | 6/2012 | Simpson et al. |
| 8,267,939 B2 | 9/2012 | Cipoletti et al. |
| 8,273,124 B2 | 9/2012 | Renganath et al. |
| 8,303,663 B2 | 11/2012 | Jimenez et al. |
| 8,353,961 B2 | 1/2013 | McClintock et al. |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,480,741 B2 | 7/2013 | Grotz et al. |
| 8,696,751 B2 | 4/2014 | Ashley et al. |
| 8,992,620 B2 | 3/2015 | Ashley et al. |
| 9,028,550 B2 | 5/2015 | Shulock et al. |
| 9,463,099 B2 | 10/2016 | Levy et al. |
| 9,687,354 B2 | 6/2017 | Bellas et al. |
| 9,913,727 B2 | 3/2018 | Thommen et al. |
| 10,307,254 B2 * | 6/2019 | Levy .................... A61F 2/2846 |
| 2001/0056302 A1 | 12/2001 | Boyer et al. |
| 2002/0128716 A1 | 9/2002 | Cohen et al. |
| 2002/0136146 A1 | 9/2002 | Lee et al. |
| 2002/0138146 A1 | 9/2002 | Jackson |
| 2002/0151976 A1 | 10/2002 | Foley et al. |
| 2003/0114899 A1 | 6/2003 | Woods et al. |
| 2003/0130739 A1 | 7/2003 | Gerbec et al. |
| 2004/0030346 A1 | 2/2004 | Frey et al. |
| 2004/0088054 A1 | 5/2004 | Berry |
| 2004/0097928 A1 | 5/2004 | Zdeblick et al. |

(56) References Cited

U.S. PATENT DOCUMENTS

| | | |
|---|---|---|
| 2004/0133273 A1 | 7/2004 | Cox |
| 2004/0153065 A1 | 8/2004 | Lim |
| 2004/0153156 A1 | 8/2004 | Cohen et al. |
| 2004/0181229 A1 | 9/2004 | Michelson |
| 2004/0186576 A1 | 9/2004 | Biscup et al. |
| 2005/0033437 A1 | 2/2005 | Bao et al. |
| 2005/0043800 A1 | 2/2005 | Paul et al. |
| 2005/0049590 A1 | 3/2005 | Alleyne et al. |
| 2005/0085910 A1 | 4/2005 | Sweeney |
| 2005/0107881 A1 | 5/2005 | Alleyne et al. |
| 2005/0113842 A1 | 5/2005 | Bertagnoli et al. |
| 2005/0197702 A1 | 9/2005 | Coppes et al. |
| 2005/0216084 A1 | 9/2005 | Fleischmann et al. |
| 2005/0229433 A1 | 10/2005 | Cachia |
| 2005/0251260 A1 | 11/2005 | Gerber et al. |
| 2005/0273169 A1 | 12/2005 | Purcell |
| 2005/0273170 A1 | 12/2005 | Navarro et al. |
| 2005/0273171 A1 | 12/2005 | Gordon et al. |
| 2006/0036259 A1 | 2/2006 | Carl et al. |
| 2006/0085073 A1 | 4/2006 | Raiszadeh |
| 2006/0089719 A1 | 4/2006 | Trieu |
| 2006/0106416 A1 | 5/2006 | Raymond et al. |
| 2006/0116767 A1 | 6/2006 | Magerl et al. |
| 2006/0142860 A1 | 6/2006 | Navarro et al. |
| 2006/0142861 A1 | 6/2006 | Murray |
| 2006/0149377 A1 | 7/2006 | Navarro et al. |
| 2006/0167547 A1 | 7/2006 | Suddaby |
| 2006/0200244 A1 | 9/2006 | Assaker |
| 2006/0235426 A1 | 10/2006 | Lim et al. |
| 2006/0235535 A1 | 10/2006 | Ferree et al. |
| 2006/0264968 A1 | 11/2006 | Frey et al. |
| 2007/0050030 A1 | 3/2007 | Kim |
| 2007/0050033 A1 | 3/2007 | Reo et al. |
| 2007/0073395 A1 | 3/2007 | Baumgartner et al. |
| 2007/0093901 A1 | 4/2007 | Grotz et al. |
| 2007/0093903 A1 | 4/2007 | Cheng |
| 2007/0123987 A1 | 5/2007 | Bernstein |
| 2007/0179611 A1 | 8/2007 | DiPoto et al. |
| 2007/0233254 A1 | 10/2007 | Grotz et al. |
| 2007/0255409 A1 | 11/2007 | Dickson et al. |
| 2007/0255413 A1 | 11/2007 | Edie et al. |
| 2007/0255415 A1 | 11/2007 | Edie et al. |
| 2007/0270961 A1 | 11/2007 | Ferguson |
| 2007/0270964 A1 | 11/2007 | Strohkirch et al. |
| 2007/0282449 A1 | 12/2007 | de Villiers et al. |
| 2007/0288092 A1 | 12/2007 | Bambakidis |
| 2008/0021555 A1 | 1/2008 | White et al. |
| 2008/0021556 A1 | 1/2008 | Edie |
| 2008/0058930 A1 | 3/2008 | Edie et al. |
| 2008/0058931 A1 | 3/2008 | White et al. |
| 2008/0065082 A1 | 3/2008 | Chang et al. |
| 2008/0065220 A1 | 3/2008 | Alleyne et al. |
| 2008/0065221 A1 | 3/2008 | Alleyne et al. |
| 2008/0077150 A1 | 3/2008 | Nguyen |
| 2008/0086276 A1 | 4/2008 | Naka et al. |
| 2008/0097441 A1 | 4/2008 | Hayes et al. |
| 2008/0103601 A1 | 5/2008 | Biro et al. |
| 2008/0114467 A1 | 5/2008 | Capote et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0161933 A1 | 7/2008 | Grotz et al. |
| 2008/0177387 A1 | 7/2008 | Parimore et al. |
| 2008/0215153 A1 | 9/2008 | Butterman et al. |
| 2008/0281424 A1 | 11/2008 | Parry et al. |
| 2008/0288073 A1 | 11/2008 | Renganath et al. |
| 2008/0300598 A1 | 12/2008 | Barreiro et al. |
| 2009/0005819 A1 | 1/2009 | Ben-Mokhtar et al. |
| 2009/0005874 A1 | 1/2009 | Fleischmann et al. |
| 2009/0012612 A1 | 1/2009 | White et al. |
| 2009/0018661 A1 | 1/2009 | Kim et al. |
| 2009/0030399 A1 | 1/2009 | Raiszadeh |
| 2009/0043312 A1 | 2/2009 | Koulisis et al. |
| 2009/0048676 A1 | 2/2009 | Fabian, Jr. |
| 2009/0105836 A1 | 4/2009 | Frey et al. |
| 2009/0143859 A1 | 6/2009 | McClellan, III et al. |
| 2009/0171389 A1 | 7/2009 | Sankaran |
| 2009/0182343 A1 | 7/2009 | Trudeau et al. |
| 2009/0204215 A1 | 8/2009 | McClintock et al. |
| 2009/0216331 A1 | 8/2009 | Grotz et al. |
| 2009/0222100 A1 | 9/2009 | Cipoletti et al. |
| 2009/0270987 A1 | 10/2009 | Heinz et al. |
| 2010/0016970 A1 | 1/2010 | Kapitan et al. |
| 2010/0057204 A1 | 3/2010 | Kadaba et al. |
| 2010/0145455 A1 | 6/2010 | Simpson et al. |
| 2010/0145456 A1 | 6/2010 | Simpson et al. |
| 2010/0249930 A1 | 9/2010 | Myers |
| 2011/0130835 A1 | 6/2011 | Ashley et al. |
| 2011/0137416 A1 | 6/2011 | Myers |
| 2011/0160861 A1 | 6/2011 | Jimenez et al. |
| 2011/0270398 A1 | 11/2011 | Grotz et al. |
| 2011/0288646 A1 | 11/2011 | Moskowitz et al. |
| 2012/0059469 A1 | 3/2012 | Myers et al. |
| 2012/0116518 A1 | 5/2012 | Grotz et al. |
| 2012/0130387 A1 | 5/2012 | Simpson et al. |
| 2012/0215316 A1 | 8/2012 | Mohr et al. |
| 2012/0245695 A1 | 9/2012 | Simpson et al. |
| 2012/0271422 A1* | 10/2012 | Miller ................ A61F 2/447 623/17.16 |
| 2012/0283830 A1 | 11/2012 | Myers |
| 2013/0096677 A1 | 4/2013 | Myers et al. |
| 2013/0158668 A1 | 6/2013 | Nichols et al. |
| 2013/0158669 A1 | 6/2013 | Sungarian et al. |
| 2013/0190875 A1 | 7/2013 | Shulock et al. |
| 2013/0197642 A1 | 8/2013 | Ernst |
| 2013/0197647 A1 | 8/2013 | Wolters et al. |
| 2013/0197648 A1 | 8/2013 | Boehm et al. |
| 2013/0204368 A1 | 8/2013 | Prevost |
| 2013/0204374 A1 | 8/2013 | Milella, Jr. |
| 2013/0253650 A1 | 9/2013 | Ashley et al. |
| 2013/0274883 A1 | 10/2013 | McLuen et al. |
| 2014/0107787 A1 | 4/2014 | Stinchfield et al. |
| 2014/0172101 A1 | 6/2014 | Glerum |
| 2014/0243983 A1 | 8/2014 | Galea et al. |
| 2014/0288652 A1 | 9/2014 | Boehm et al. |
| 2014/0316522 A1 | 10/2014 | Weiman et al. |
| 2014/0358246 A1 | 12/2014 | Levy et al. |
| 2014/0364951 A1 | 12/2014 | De Villiers et al. |
| 2015/0025634 A1 | 1/2015 | Boehm et al. |
| 2015/0094814 A1 | 4/2015 | Emerick et al. |
| 2015/0223946 A1 | 8/2015 | Weiman et al. |
| 2015/0257894 A1* | 9/2015 | Levy ................ A61F 2/442 623/17.15 |
| 2015/0351925 A1 | 12/2015 | Emerick et al. |
| 2015/0374512 A1 | 12/2015 | Glerum et al. |
| 2016/0089247 A1 | 3/2016 | Nichols et al. |
| 2016/0095718 A1 | 4/2016 | Burkhardt et al. |
| 2016/0199195 A1 | 7/2016 | Hauck et al. |
| 2017/0000627 A1 | 1/2017 | Levy et al. |
| 2017/0100255 A1 | 4/2017 | Hleihil et al. |
| 2017/0119543 A1 | 5/2017 | Dietzel et al. |
| 2017/0172760 A1 | 6/2017 | Oebl et al. |
| 2017/0224506 A1 | 8/2017 | Ashley et al. |
| 2017/0231778 A1 | 8/2017 | Overes et al. |
| 2017/0252178 A1 | 9/2017 | Moskowitz et al. |
| 2017/0290671 A1 | 10/2017 | Milz et al. |
| 2017/0290680 A1 | 10/2017 | Pinal et al. |
| 2017/0312092 A1 | 11/2017 | Link et al. |
| 2017/0325967 A1 | 11/2017 | Link et al. |
| 2017/0333198 A1 | 11/2017 | Robinson |
| 2017/0333199 A1 | 11/2017 | Sharifi-Mehr et al. |
| 2017/0367842 A1 | 12/2017 | Predick et al. |
| 2018/0000606 A1 | 1/2018 | Hessler et al. |
| 2018/0000609 A1 | 1/2018 | Hessler et al. |
| 2018/0014947 A1 | 1/2018 | Baynham |
| 2018/0071111 A1 | 3/2018 | Sharifi-Mehr et al. |
| 2018/0110628 A1 | 4/2018 | Sharifi-Mehr et al. |
| 2018/0116819 A1 | 5/2018 | Maguire et al. |
| 2018/0125671 A1 | 5/2018 | Bernard et al. |

(56) References Cited

U.S. PATENT DOCUMENTS

| | | | |
|---|---|---|---|
| 2018/0235769 | A1 | 8/2018 | Levy et al. |
| 2018/0243107 | A1 | 8/2018 | Foley et al. |

FOREIGN PATENT DOCUMENTS

| | | | |
|---|---|---|---|
| CN | 101631516 | A | 1/2010 |
| CN | 101686860 | A | 3/2010 |
| CN | 101686865 | B | 5/2013 |
| EP | 1442715 | A3 | 11/2004 |
| EP | 1415624 | B1 | 5/2006 |
| JP | 2001-518824 | A | 10/2001 |
| JP | 2008-502372 | A | 1/2008 |
| JP | 2015533337 | A | 11/2015 |
| WO | 2003003951 | A1 | 1/2003 |
| WO | 2004016250 | A1 | 2/2004 |
| WO | 2004016205 | A3 | 5/2004 |
| WO | 2006044786 | A3 | 1/2007 |
| WO | 2008011371 | A3 | 3/2008 |
| WO | 2007124078 | A3 | 7/2008 |
| WO | 2008039811 | A3 | 7/2008 |
| WO | 2008112607 | A3 | 12/2008 |
| WO | 2008148210 | A1 | 12/2008 |
| WO | 2009033100 | A1 | 3/2009 |
| WO | 2008121251 | A3 | 8/2009 |
| WO | 2009064787 | A3 | 8/2009 |
| WO | 2009105182 | A1 | 8/2009 |
| WO | 2009114381 | A1 | 9/2009 |
| WO | 2008086276 | A3 | 12/2009 |
| WO | 2010074704 | A1 | 7/2010 |
| WO | 2010068725 | A3 | 10/2010 |
| WO | 2011011609 | A3 | 6/2011 |
| WO | 2011150077 | A1 | 12/2011 |
| WO | 2014071268 | A1 | 5/2014 |
| WO | 2016183382 | A1 | 11/2016 |
| WO | 2017117513 | A1 | 7/2017 |

OTHER PUBLICATIONS

Extended European Search Report for Application No. 14159365.7 dated Jun. 18, 2014.
Extended European Search Report for Application No. EP 17198694.6 dated Mar. 15, 2018, 7 pages.
Extended European Search Report for Application No. EP14159619 dated Jun. 12, 2014.
International Search Report and Written Opinion dated Jun. 5, 2009 for related PCT/US2009/000974.
International Search Report and Written Opinion dated Aug. 13, 2010, in related International Application No. PCT/US2009/067446 filed Dec. 10, 2009.
International Search Report and Written Opinion dated Jun. 30, 2009, in related International Application No. PCT/US2008/003776 filed Mar. 21, 2008.
International Search Report and Written Opinion dated Nov. 11, 2010, in International Application No. PCT/US2010/031247 entitled "Insertion Handle for Implant."
International Search Report and Written Opinion dated Sep. 22, 2011 in related International Application No. PCT/US2011/037929.
Japanese Office Action for Application No. 2013-512209 dated Jan. 27, 2015.
Sharifi-Mehr et al., U.S. Appl. No. 15/702,171, filed Sep. 12, 2017, titled "Interbody Implant with Independent Control of Expansion at Multiple Locations".
Office Action issued for corresponding Japanese Patent Application No. 2017-207035 dated Aug. 26, 2022.

* cited by examiner

EXPANDABLE INTERBODY IMPLANT WITH LATERAL ARTICULATION

CROSS-REFERENCE TO RELATED APPLICATIONS

This application is a continuation of U.S. patent application Ser. No. 16/662,187, filed Oct. 24, 2019 which is a continuation of U.S. patent application Ser. No. 15/794,693 filed Oct. 26, 2017, now U.S. Pat. No. 10,485,675, which claims the benefit of the filing date of U.S. Provisional Patent Application No. 62/413,038 filed Oct. 26, 2016, the disclosures of which are hereby incorporated herein by reference.

BACKGROUND OF THE INVENTION

Intervertebral implants are commonly used in spinal surgery, such as in interbody fusion procedures, in which an implant (e.g., a spacer or cage) is placed in the disc space between two vertebrae to be fused together. At least a portion of the disc is typically removed before the implant is positioned in the intervertebral space, and the implant may be supplemented with bone graft material to promote fusion of the vertebrae. Interbody fusion procedures may also be performed in conjunction with other types of fixation, such as pedicle screw fixation, to provide additional stability, particularly while the vertebrae fuse together.

Different interbody fusion procedures can be distinguished by their location along the spine (e.g., in the cervical, thoracic, or lumbar regions); by the type of implant used; and by the surgical approach to the intervertebral space, in which different surgical approaches often imply different structural characteristics of the implant or implants used. Different surgical approaches to the spine include anterior, posterior, and lateral. Examples of interbody fusion techniques performed along a posterior approach include posterior lumbar interbody fusion (PLIF) and transforaminal lumbar interbody fusion (TLIF). PLIF techniques typically include positioning two intervertebral implants into the intervertebral space along a posterior to anterior direction, with one implant being positioned towards the left side of the spine and one implant being positioned towards the right side of the spine. The implants used in such PLIF techniques typically have a straight shape, in that they extend along a central axis. TLIF techniques, by contrast, typically include positioning one intervertebral implant into the intervertebral space (often towards the anterior portion of the intervertebral space) from the posterior of the patient, but the spine is approached on one side from a more lateral position than in PLIF techniques. The implants used in such TLIF techniques are often curved, such that they have an overall kidney bean-like shape. Interbody fusion techniques performed along a lateral approach, on the other hand, often involve implants that are generally symmetric along their linear longitudinal axis (e.g., having a substantially rectangular or oval shape), but the implants are typically larger than those used in PLIF or TLIF techniques. That is, intervertebral implants used in lateral approaches often cover a substantial portion of the disc space.

Included among the different types of intervertebral implants are expandable implants. Such implants often have an initially contracted configuration, such that they have a low profile in the superior-inferior direction, in order to ease insertion into the intervertebral space. Such expandable implants can then be expanded in the superior-inferior direction after implantation, so as to securely engage and stabilize the vertebrae on both sides of the intervertebral space. Examples of expandable intervertebral implants are disclosed in U.S. Pat. No. 8,992,620 ("the '620 Patent") and in U.S. Patent Application Publication No. 2017/0290671 (hereinafter "the '671 Publication"), the disclosures of which are hereby incorporated by reference herein as if fully set forth herein.

Although considerable effort has been devoted in the art to optimization of such intervertebral systems and methods, still further improvement would be desirable.

BRIEF SUMMARY OF THE INVENTION

The present invention relates to interbody implants, as well as to systems comprising the same. The present invention also relates to associated methods of performing spinal interbody fusion procedures using such implants and systems.

One aspect of the present invention provides a spinal implant. The spinal implant in accordance with this aspect of the invention preferably includes a body having a first surface for contacting a first vertebral body and at least two extendable support elements connected to the body at respective locations. The spinal implant may include an input for expanding the extendable support elements, such that the extendable support elements each apply a respective expansion force directed away from the first surface. Desirably, the spinal implant may be configured such that application of a single input force to the input induces the extendable support elements to apply different amounts of expansion force.

In accordance with some further aspects of the above spinal implant, the extendable support elements may include pistons slidably received within respective cylinders. Such extendable support elements may be driven by hydraulic fluid supplied to the input. In accordance with some yet further aspects of the spinal implant, the pistons may have different cross-sectional areas from one another. According to some even further aspects, the spinal implant may include two portions articulatable about a hinge portion. In accordance with some of such aspects, a first piston with a larger cross-sectional area may be located on the hinge portion. In some even further aspects, a second piston with a smaller cross-sectional area may be located on one of the two articulatable portions. Some even further aspects may include a third piston slidably received within a third cylinder on the other of the two articulatable portions. In some of such aspects, the first piston may have a larger cross-sectional area than both of the second and third pistons. In accordance with other aspects of the spinal implant, the extendable support elements may be driven by hydraulic fluid supplied to the input, where the input is located on one of the articulatable portions opposite the hinge portion. In accordance with some of such aspects, the spinal implant may be configured to direct the hydraulic fluid from the input on one of the articulatable portions to the other of the articulatable portions via the hinge portion. In accordance with yet other aspects of the spinal implant, the articulatable portions may include at least three segments, where a first one of the segments is articulatably connected to a second one of the segments, and a third one of the segments is articulatably connected to the second segment, with the second segment being located between the first and third segments. In such aspects, the first piston with the larger cross-sectional area may be located on the second segment.

Another aspect of the present invention provides a spinal implant. The spinal implant in accordance with this aspect of the invention preferably includes first and second portions connected together by a first hinge for articulation about the hinge. Desirably, the first hinge may include first and second rigid links each pivotably connected to the first and second portions of the implant.

In accordance with some further aspects of the above spinal implant, the spinal implant may be expandable along the longitudinal axis of the spine. In some of such aspects, the expansion of the spinal implant may be driven by supplying a hydraulic fluid to the implant. In some even further of such aspects, a piston slidably received within a cylinder may be provided on each of the first and second portions of the implant. In some aspects of the invention, the spinal implant may be configured to direct the hydraulic fluid from between the first and second portions of the implant via at least one of the first and second rigid links.

In accordance with other further aspects of the above spinal implant, the spinal implant may include a third portion connected to the second portion by a second hinge for articulation about the second hinge. Desirably, the second hinge may include third and fourth rigid links each pivotably connected to the second and third portions of the implant. In accordance with other aspects of the spinal implant, the first hinge is configured to allow the first and second portions to articulate into an arrangement such that the longitudinal axes of the first and second portions are coincident with one another.

In accordance with some further aspects of the above spinal implant, the first and second rigid links may each be pivotably connected to the first and second portions of the implant such that the rigid links are positioned on respective longitudinal sides of the implant. In accordance with other further aspects of the spinal implant, the first and second rigid links may each be pivotably connected to the first and second portions of the implant such that the rigid links cross from one longitudinal side of the implant to the other side between each pivotably connected end of the respective link. In some of such aspects, one of the links may have a bent profile.

Another aspect of the present invention provides a spinal implant. The spinal implant in accordance with this aspect of the invention preferably includes first and second portions connected together by a hinge for articulation about the hinge. The hinge desirably includes a first rigid link pivotably connected to the first and second portions of the implant. Preferably, the first rigid link has a passageway therein for communicating a hydraulic fluid between the first and second portions of the spinal implant.

In accordance with some further aspects of the above spinal implant, the spinal implant may be expandable along the longitudinal axis of the spine. In some of such aspects, the expansion of the spinal implant may be driven by supplying a hydraulic fluid to the implant. In some even further of such aspects, a piston slidably received within a cylinder may be provided on each of the first and second portions of the implant.

In accordance with other further aspects of the above spinal implant, the hinge may include a second rigid link pivotably connected to the first and second portions of the implant. In some of such aspects, the second rigid link may have a passageway therein for communicating the hydraulic fluid between the first and second portions of the spinal implant. In accordance with some even further aspects, the first and second rigid links may each be pivotably connected to the first and second portions of the implant such that the rigid links are positioned on respective longitudinal sides of the implant. In accordance with other further aspects, the first and second rigid links may each be pivotably connected to the first and second portions of the implant such that the rigid links cross from one longitudinal side of the implant to the other side between each pivotably connected end of the respective link. In some of such aspects, one of the links may have a bent profile.

Another aspect of the present invention provides a spinal implant. The spinal implant in accordance with this aspect of the invention preferably includes a body having a first surface and a piston slidably received within a cylinder of the body. The piston may be slidable along an expansion axis of the cylinder so as to translate a second surface away from the first surface. Desirably, the spinal implant is configured to rotate the piston as the piston slides along the expansion axis. In accordance with some aspects of such spinal implant, the rotation of the piston may be controlled by a cam. In one example, the cam may be provided on an exterior surface of the piston such that the cam is engageable by a follower coupled to the cylinder. In accordance with other aspects of the invention, a ratcheting component may constrain the rotation of the piston to a first direction as the piston slides along the expansion axis. The ratcheting component may be configured to be disabled, when desired, so as to permit the piston to rotate in a second direction opposite the first direction. In accordance with yet other aspects of such spinal implant, the piston may be coupled to an engagement plate having a second surface arranged to contact a second vertebral body. Desirably, the engagement plate may be coupled to the piston by a rotatable connection and/or a pivotable connection.

Another aspect of the present invention provides a spinal implant. The spinal implant in accordance with this aspect of the invention preferably includes a body having a first surface and at least one extendable support element connected to the body. The extendable support element may be configured to expand from a contracted configuration to at least one extended configuration to translate a second surface away from the first surface. The spinal implant in accordance with this aspect of the invention preferably also includes a locking system advanceable among a plurality of successive locked configurations, where each successive locked configuration corresponds to a successive level of expansion of the extendable support element. Desirably, the locking system prevents movement of the extendable support element towards the contracted configuration when the locking system is positioned in one of the locked configurations. Moreover, the positioning of the locking system into each of the successive locked configurations is preferably performed via operation of a cam.

In accordance with some further aspects of the above spinal implant, the cam may be provided on an exterior surface of the extendable support element such that the cam is engageable by a follower coupled to the body. In accordance some such aspects of the invention, the engagement between the follower and the cam may induce rotation of the extendable support element.

In accordance with other further aspects of the spinal implant, a ratcheting component may prevent the locking system from reverting to a preceding locked configuration. In some such aspects, the ratcheting component may be configured to be disabled, when desired, so as to permit movement of the extendable support element to the contracted configuration.

In accordance with yet other further aspects of the above spinal implant, the locking system may include a tiered array of upper steps engageable with a tiered array of lower steps at a plurality of discrete positions as the extendable support element expands to the at least one extended configuration. In accordance with other further aspects of the spinal implant, the extendable support element may include a piston slidably received within a cylinder coupled to the body.

Another aspect of the present invention provides a spinal implant system. The spinal implant system in accordance with this aspect of the invention preferably includes a spinal implant and a tool connectable thereto. The spinal implant may include first and second portions connected together by a hinge for articulation about the hinge, and the tool may include a spreader for spreading apart the first and second portions of the spinal implant about the hinge. The hinge may be located at the distal end of the spinal implant, and a tool interface for connection to the tool may be located at the proximal end of the spinal implant.

In accordance with some further aspects of the above spinal implant, the spreader may be insertable into a space defined between the first and second portions in order to spread apart those portions. In accordance with some of such aspects, movement of the spreader from the distal end towards the proximal end of the spinal implant may induce the spreading apart of the first and second portions of the implant. In accordance with some even further aspects, the spreader may include at least one ramp surface engageable with at least one of the first and second portions of the implant during movement of the spreader from the distal end towards the proximal end, so as to induce the spreading apart of the first and second portions of the implant.

In accordance with other further aspects of the above spinal implant, the spinal implant may be expandable along the longitudinal axis of the spine. That expansion of the spinal implant along the longitudinal axis of the spine may be controlled by the tool. For example, a hydraulic fluid may be supplied through the tool to a port at the proximal end of the spinal implant. In accordance with some aspects of the invention, the spinal implant may include a first piston expandable by the hydraulic fluid, which piston may be located on the hinge. In some of such aspects of the invention, the spinal implant may include a second piston expandable by the hydraulic fluid, which second piston may be located on one of the first and second portions of the spinal implant. In some even further aspects, the spinal implant may include a third piston expandable by the hydraulic fluid, where the second piston is located on one of the first and second portions of the implant and the third piston is located on the other portion. In accordance with some aspects of the invention, the first piston on the hinge may have a larger cross-sectional area than the second piston on one of the first and second portions of the implant. In accordance with some other aspects, the port for the hydraulic fluid may be disposed on the first portion of the spinal implant. In accordance with some of such aspects, the spinal implant may be configured to direct the hydraulic fluid from the port in the first portion to the second portion through the hinge.

Another aspect of the present invention provides a method of performing a spinal interbody fusion procedure. The method in accordance with this aspect of the invention preferably includes inserting an implant into an intervertebral space between a first vertebral body and a second vertebral body of a spine using a tool connected to a proximal end of the implant. The method also desirably includes spreading first and second articulatable portions of the implant apart about a hinge at a distal end of the implant using the tool while the tool is connected to the proximal end of the implant.

In accordance with some further aspects of the above method, the step of spreading the first and second articulatable portions of the implant apart using the tool may include inserting a spreading component into a space defined between the first and second articulatable portions of the implant. In some of such aspects, the step of spreading the first and second articulatable portions of the implant apart may include longitudinally advancing the spreader from the proximal end towards the distal end of the implant.

In accordance with other further aspects, the method may further include the step of expanding the implant along the longitudinal axis of the spine. In some of such aspects, the expanding step may be actuated by the tool. In some further aspects, the expanding step may include supplying a hydraulic fluid to the implant via the tool. In some even further aspects, the hydraulic fluid may flow between the first and second articulatable portions of the implant through the hinge. In some other aspects, the method may further include the step of expanding first and second pistons disposed on the respective first and second articulatable portions using the hydraulic fluid. In some other aspects, the expanding step may include applying a pressure to the hydraulic fluid. In some of such aspects, the application of the pressure to the hydraulic fluid may result in the first and second pistons applying respective first and second expansion forces between the first and second vertebral bodies, where the first and second expansion forces are different from one another.

DETAILED DESCRIPTION

When referring to specific directions in the following disclosure, it should be understood that, as used herein, the term "proximal" means closer to the operator/surgeon, and the term "distal" means further away from the operator/surgeon. The term "anterior" means toward the front of the body or the face, and the term "posterior" means toward the back of the body. With respect to the longitudinal axis of the spine, the term "superior" refers to the direction towards the head, and the term "inferior" refers to the direction towards the pelvis and feet. Finally, the term "lateral" or "laterally," as used below, refers to a direction or movement that is in the transverse plane, which is orthogonal to the longitudinal axis of the spine.

Figure 1:
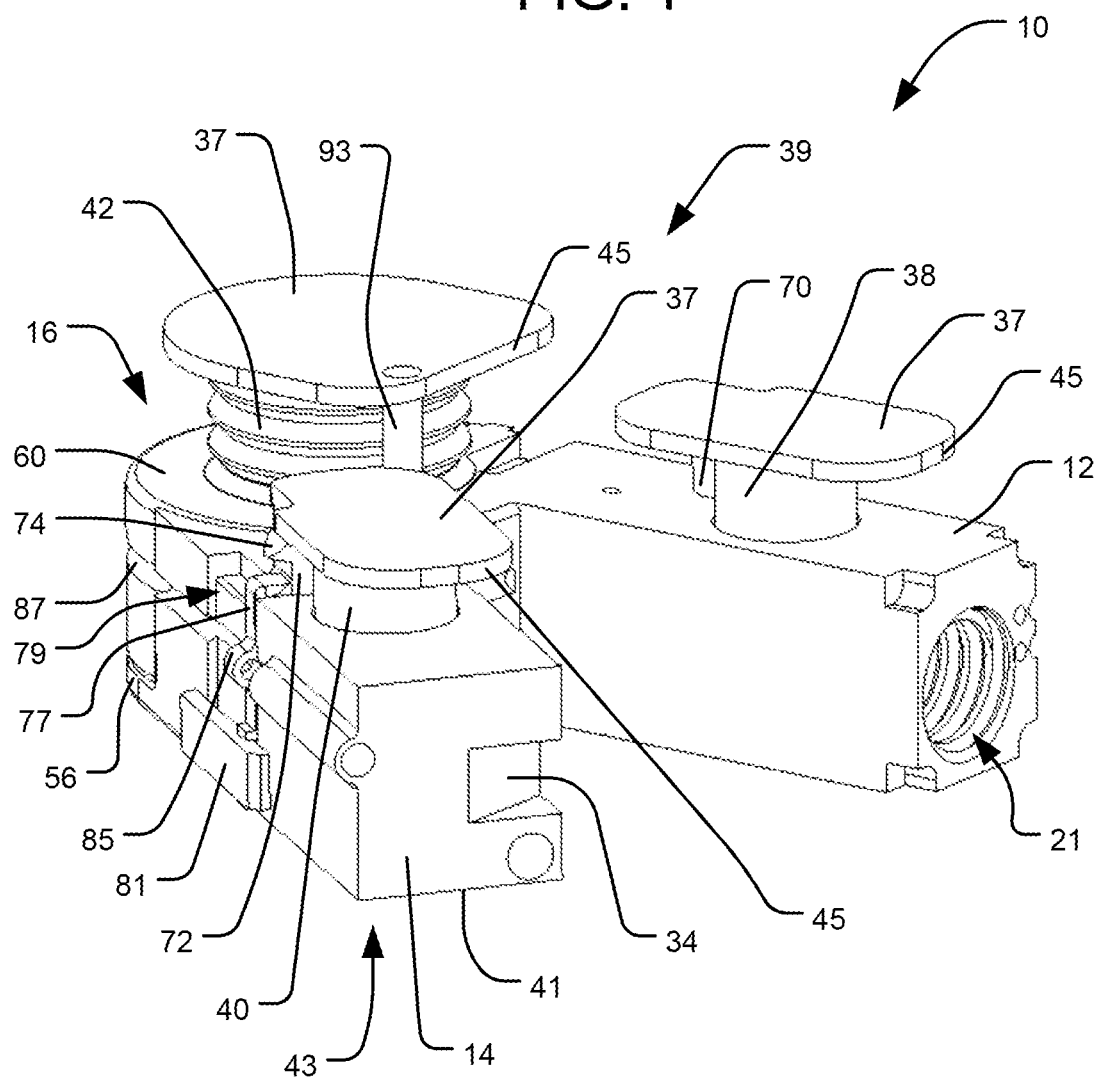
FIG. 1. is a perspective view of a spinal implant in accordance with an embodiment of the present invention.
Figure 2A:
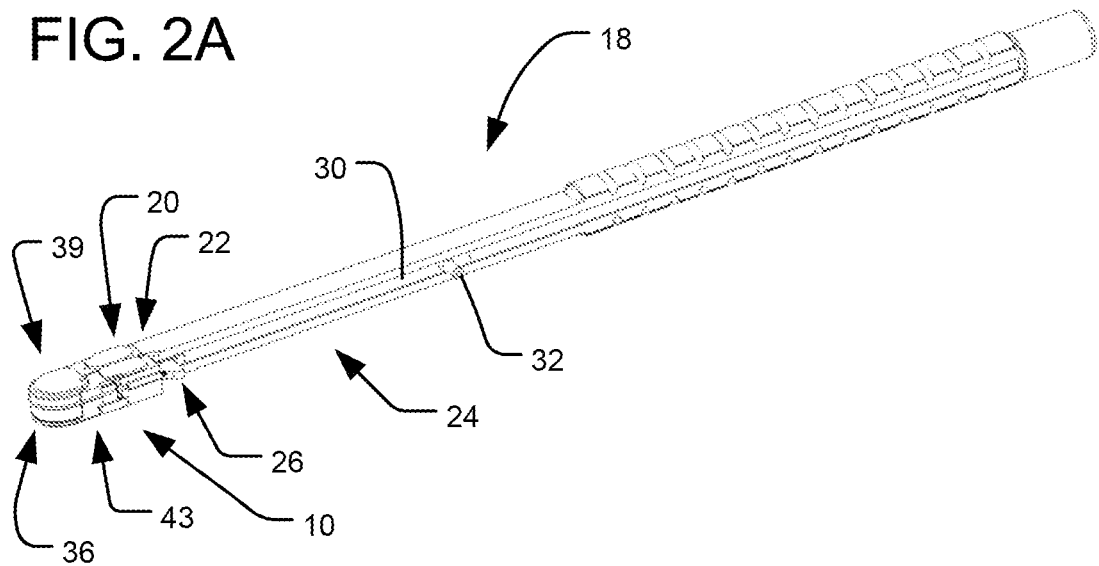
FIG. 2A is a perspective view of the spinal implant of FIG. 1 connected to a delivery tool.
Figure 2B:
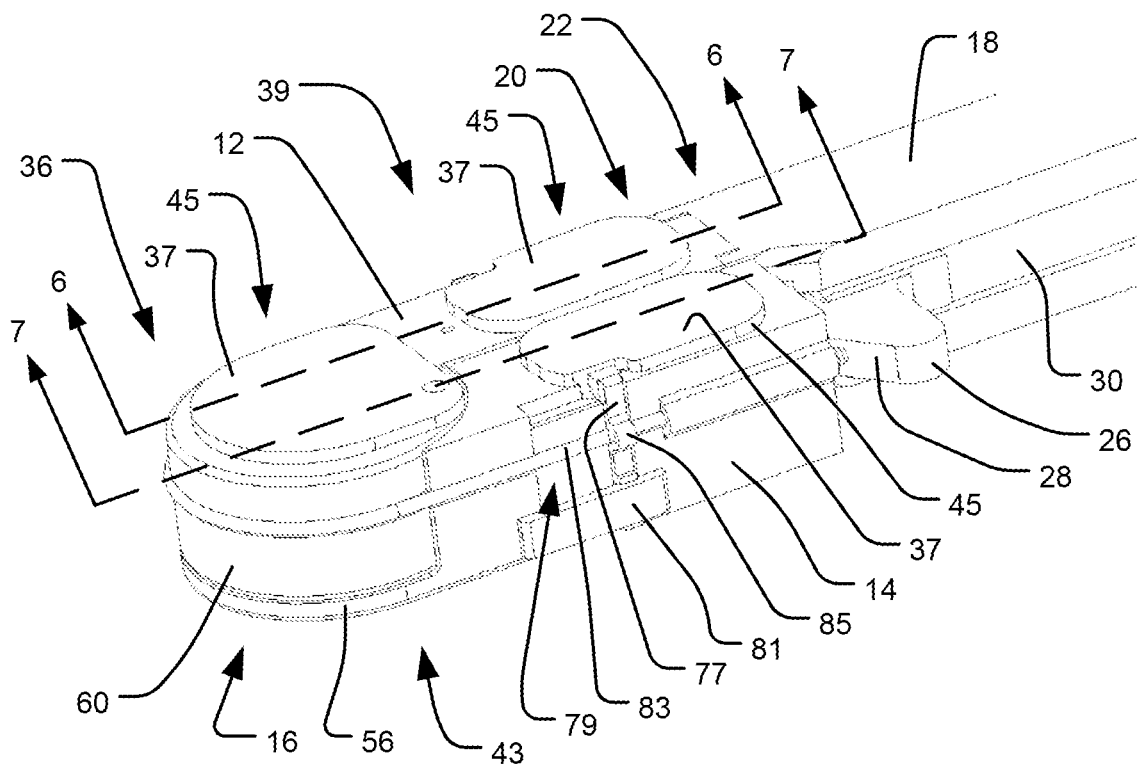
FIG. 2B is an enlarged view of FIG. 2A, focusing on the spinal implant and delivery tool connection.
Figure 3A:
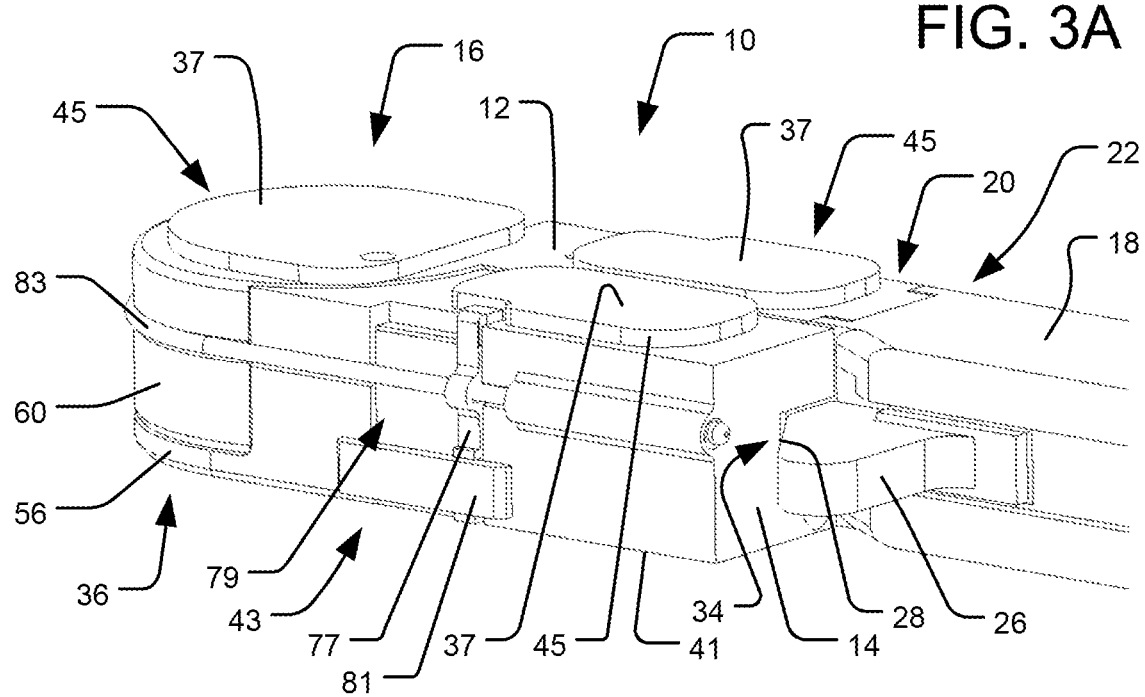
FIG. 3A is a perspective view of the spinal implant of FIG. 1 in a closed configuration and connected to a delivery tool.
Figure 3B:
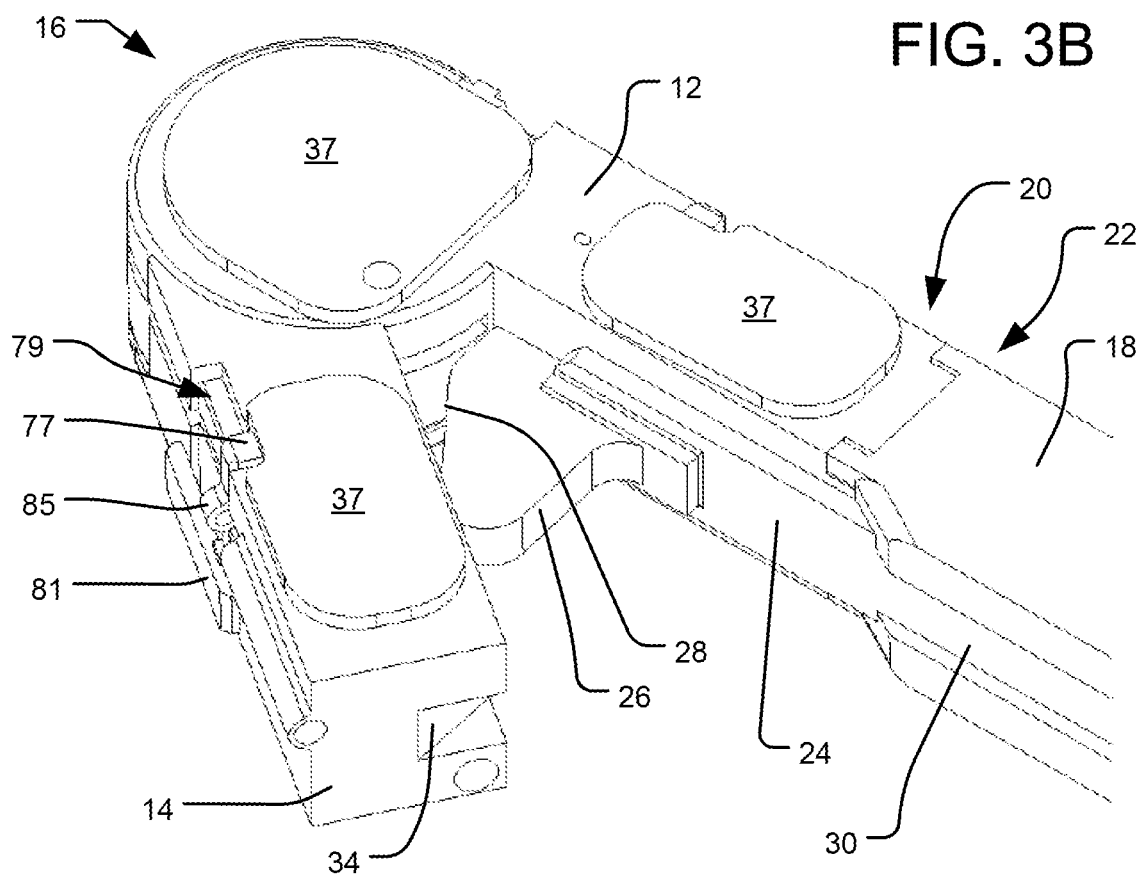
FIG. 3B is a perspective view of the spinal implant of FIG. 1 in a laterally expanded configuration and connected to the delivery tool.
Figure 4A:
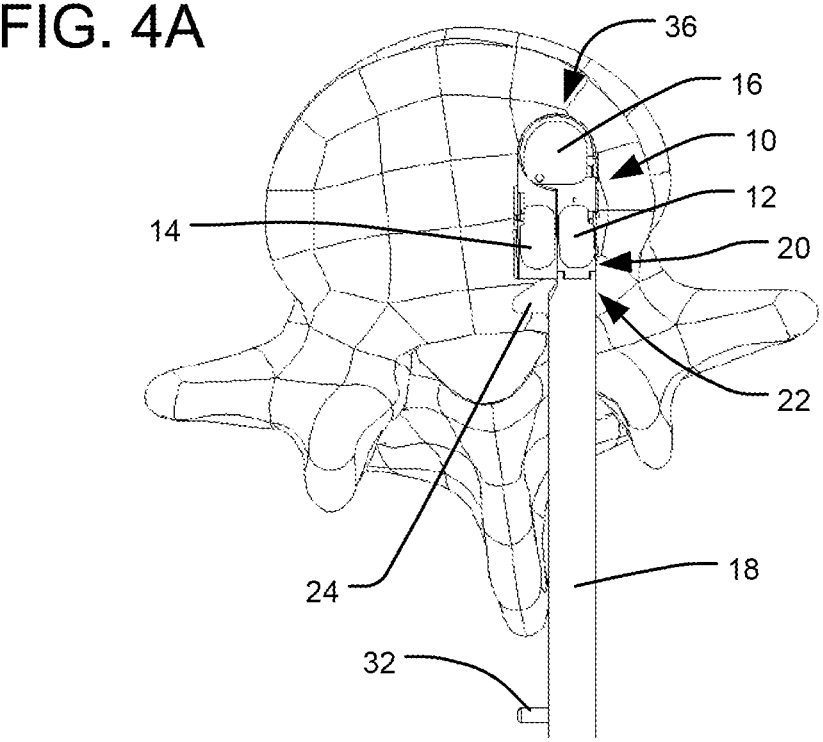
FIG. 4A is a top plan view of the spinal implant of FIG. 1 in the closed configuration, connected to the delivery tool, and positioned in an intervertebral space.
Figure 4B:
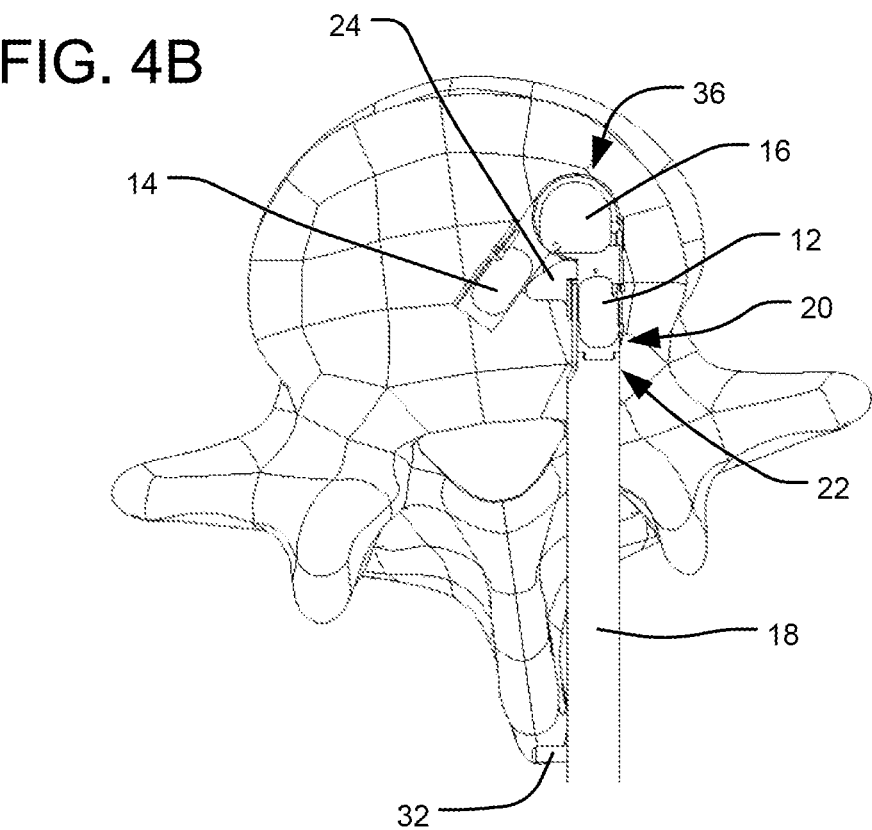
FIG. 4B is a top plan view of the spinal implant of FIG. 1 in the laterally expanded configuration, connected to the delivery tool, and positioned in the intervertebral space.

FIG. 1 illustrates an implant 10 in accordance with one embodiment of the present invention. The implant 10 includes two segments articulatable with respect to one another, in the form of a first arm 12 and a second arm 14. Specifically, the first and second arms 12, 14 are connected together by a hinge portion 16. The implant 10 is insertable into an intervertebral space in a closed configuration, as illustrated in FIGS. 2A-3A and 4A, and the implant 10 can be expanded laterally within the intervertebral space by articulating the arms 12, 14 apart about the hinge portion 16, as shown in FIGS. 3B and 4B.

The insertion of the implant 10 into the intervertebral space can be performed by a delivery tool 18 securely attachable to the proximal end 20 of the implant 10 via an anchor located on the implant 10. The anchor may be in the form of a threaded bore 21 for receiving a correspondingly threaded portion at the distal end 22 of the delivery tool 18, and the threaded bore 21 may be located on the first arm 12. The delivery tool 18 may also be responsible for expanding the implant 10 laterally. For example, as shown in FIGS. 2A-B, the distal end 22 of the delivery tool 18 may include a spreader 24 having a tab 26 with an angled distal surface 28. The spreader 24 may be guided for longitudinal movement with respect to the delivery tool 18 by a track 30, and that longitudinal movement of the spreader 24 may be controlled by a control arm 32 towards the proximal end of the spreader 24. The control arm 32 may be directly grasped by a surgeon and pushed distally or pulled proximally in order to induce corresponding longitudinal movement of the spreader 24 with respect to the delivery tool 18, or the control arm 32 may be engaged by another component (e.g., a proximally extending control cable) that can be advanced or retracted in order to induce the longitudinal movement of the spreader 24. As shown in FIG. 3A, the angled distal surface 28 of the spreader 24 is configured to contact an engagement surface 34 of the implant when the spreader 24 is advanced distally, such that the distal movement of the angled distal surface 28 pushes on the engagement surface 34 and causes the second arm 14 to articulate with respect to the first arm 12 about the hinge portion 16, which may be located at the distal end 36 of the implant 10. As shown in FIGS. 1 and 3B, the engagement surface 34 may be angled, for example by having an angle that matches the angle of the angled distal surface 28 of the spreader 24.

Figure 5A:
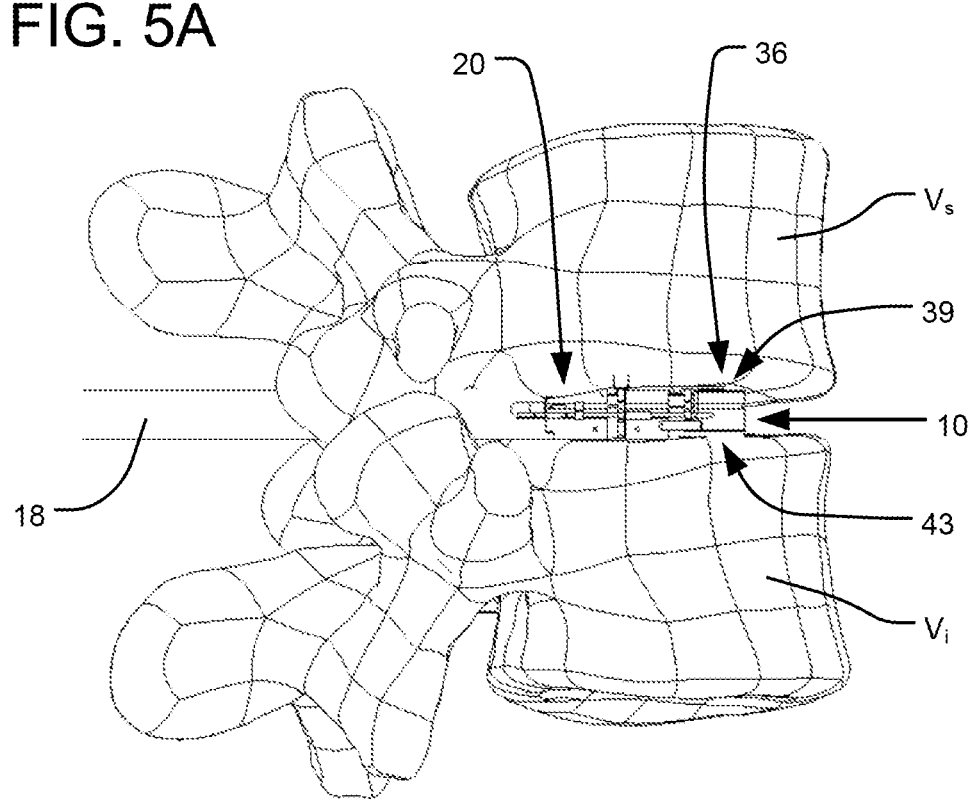
FIG. 5A is a side elevational view of the spinal implant of FIG. 1 positioned in an intervertebral space in a longitudinally contracted configuration.
Figure 5B:
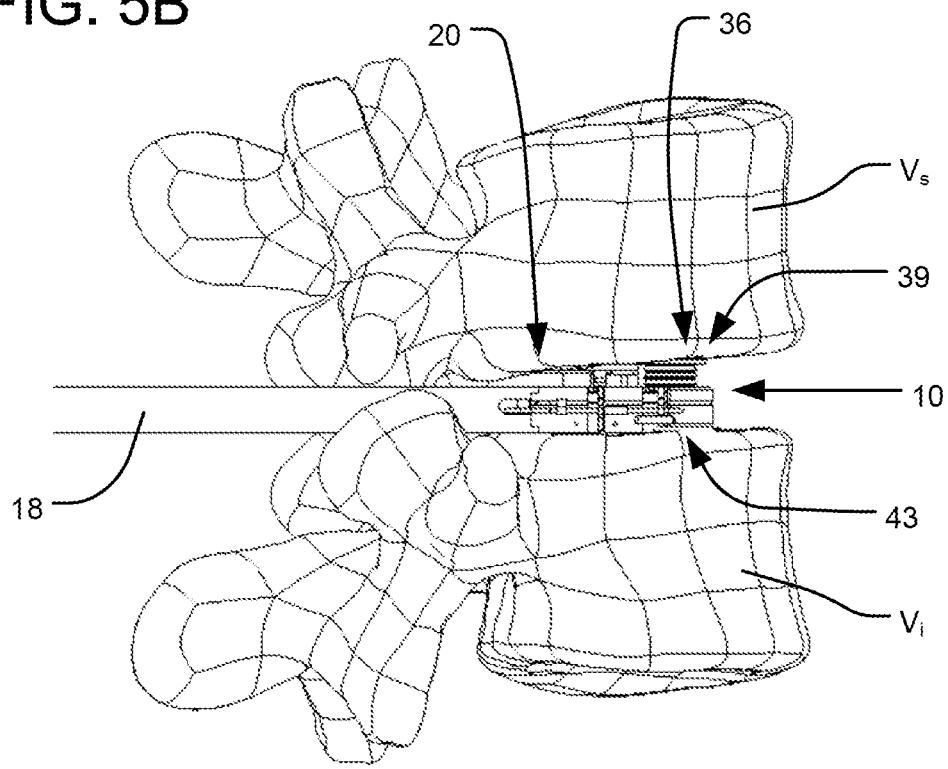
FIG. 5B is a side elevational view of the spinal implant of FIG. 1 positioned in the intervertebral space in a longitudinally expanded configuration.

After the implant 10 has been laterally expanded to the desired configuration, the implant 10 can also be expanded longitudinally in the superior-inferior direction, as shown in FIG. 5B. Specifically, the implant 10 can be expanded such that one or more upper vertebral engaging surfaces 37 on the top end 39 of the implant 10 are moved apart from one or more lower vertebral engaging surfaces 41 on the bottom end 43 of the implant 10. Such longitudinal expansion can cause the implant 10 to securely engage the vertebral body $V_s$ in the superior direction and the vertebral body $V_i$ in the inferior direction, and further expansion can result in some movement of the superior vertebral body $V_s$ and the inferior vertebral body $V_i$ away from one another, such that at least some distraction of the intervertebral space results.

The longitudinal expansion of the implant may be performed using various means, including bellows, rotating cam lift mechanisms, rotating screw lift mechanisms, or other such devices, as disclosed in the '620 Patent. The longitudinal expansion may also be driven by hydraulics, as disclosed in the '620 Patent and the '671 Publication, and as discussed below in connection with the various illustrated embodiments. For example, the implant 10 may include one or more pistons received within associated cylinders and driven to translate outwardly along the longitudinal axis of the spine by hydraulic pressure, thus resulting in longitudinal expansion of the implant. The pistons may have plate portions 45 at their top ends that may include the upper vertebral engaging surfaces 37 thereon for contacting and applying expansion force to the superior vertebral body $V_s$. Alternatively, the top ends of the pistons may simply be defined as the upper vertebral engaging surfaces 37 and configured to directly engage the superior vertebral body $V_s$. Although not shown in the drawings herein, the vertebral engaging surfaces of the embodiments disclosed herein may be smooth surfaces, or they may include textural features (e.g., protrusions, ridges, etc.) for more securely interfacing with the engaged vertebrae, or they may include spikes or similar features (which can either be fixed or deployable after implantation) for penetrating into the engaged vertebrae.

As shown in the embodiment of FIGS. 1-9, the implant 10 may include a first piston 38 on the first arm 12, a second piston 40 on the second arm 14, and a central piston 42 at the hinge portion 16. The pistons may be individually controlled via separate hydraulic pressure channels formed within the implant, or, as in the embodiment of FIGS. 1-9, they may be controlled by a common hydraulic pressure channel. Specifically, a channel 44 formed within the first arm 12 may communicate with the cylinder 46 within which the first piston 38 is disposed. That way, hydraulic fluid within the channel 44 may cause outward expansion of the first piston 38. A seal member, which may be in the form of an o-ring 47a, may be provided between the first piston 38 and the associated cylinder 46, so that those components can slide with respect to one another while preventing hydraulic fluid from escaping at that interface. The channel 44 may communicate with an opening so as to be supplied with pressurized hydraulic fluid from the delivery tool 18. For example, the channel 44 may communicate with the bore 21, so that the hydraulic fluid may be supplied to the channel 44 by a conduit 48 in the delivery tool 18. The supply for the hydraulic fluid need not be provided through the same bore 21 used to anchor the implant 10 to the delivery tool 18, however, and alternative embodiments may, for example, include a separate opening in the outer surface of the implant for communication with a conduit 48 of the delivery tool 18.

The channel 44 may also communicate with the cylinder 50 within which the central piston 42 is disposed, so that the hydraulic fluid may also cause outward expansion of the central piston 42. The communication between the channel 44 and the cylinder 50 may either be direct communication or communication via an intervening pathway, such as via angled channel 52 illustrated in FIG. 6. Channel 52 may be formed by drilling an angled bore from outside the first arm 12 to the distal end of the cylinder 50, such that the bore intersects the channel 44. If formed in that manner, the extraneous end 54 of the channel 52 may subsequently be plugged, so that the hydraulic fluid does not escape the implant 10 via that path. A seal member, which may be in the form of an o-ring 47b, may be provided between the central piston 42 and the associated cylinder 50, so that those components can slide with respect to one another while preventing hydraulic fluid from escaping at that interface.

Figure 7:
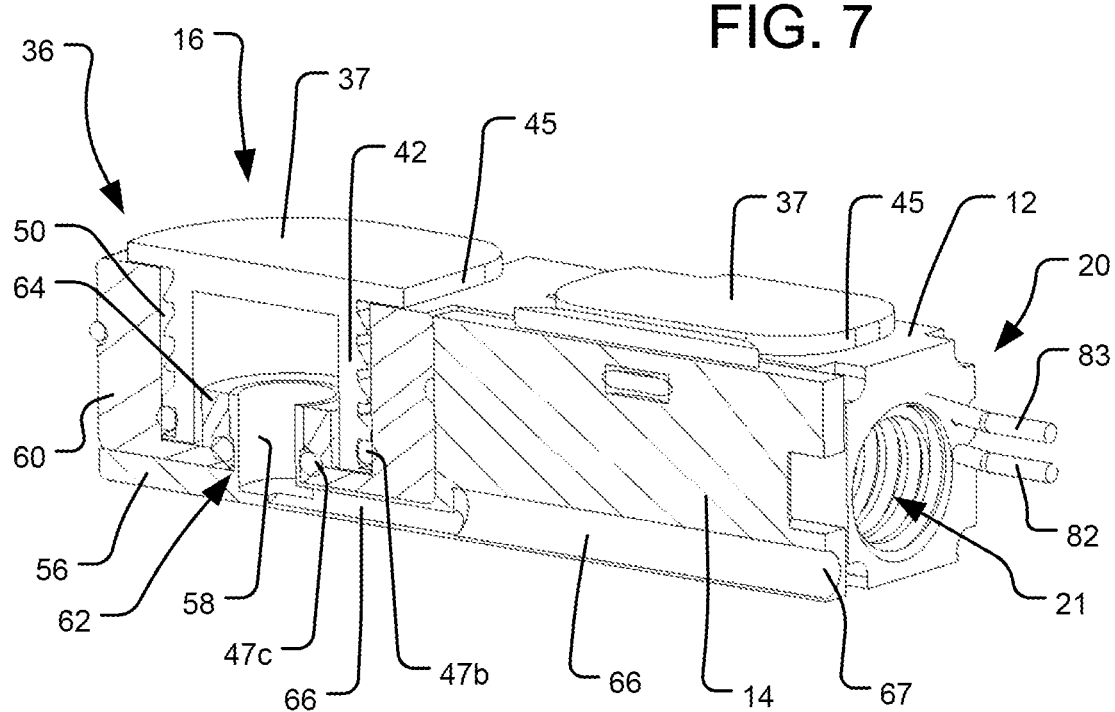
FIG. 7 is a perspective cross-sectional view of the spinal implant of FIG. 1, taken along line 7-7 in FIG. 2B.
Figure 8:
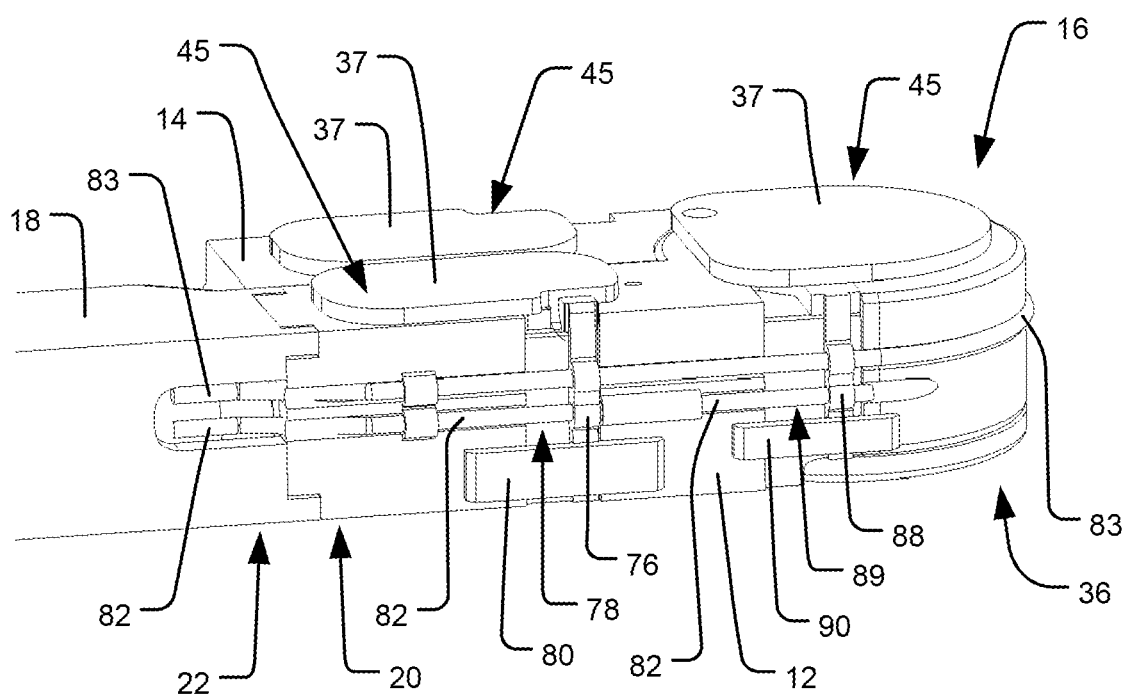
FIG. 8 is a perspective view of the spinal implant of FIG. 1 connected to the delivery tool.
Figure 9:
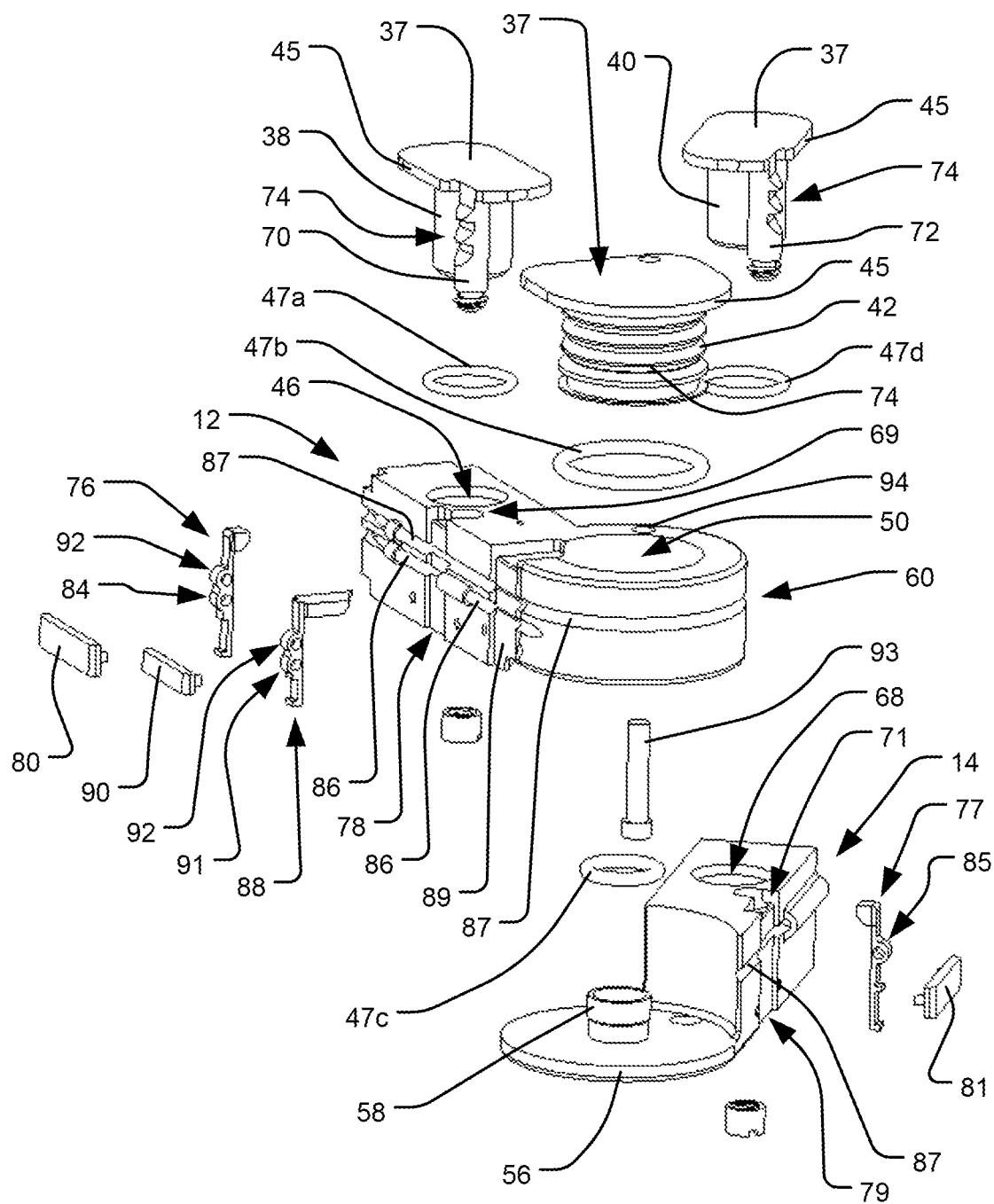
FIG. 9 is an exploded perspective view of the spinal implant of FIG. 1.

The articulating connection between the first arm 12 and the second arm 14 at hinge portion 16 may be constructed so as to allow for the communication of the hydraulic fluid between the first arm 12 and the second arm 14. For example, as shown in FIG. 9, the second arm 14 includes a circular plate 56 at the distal end 36 of the implant 10. That circular plate includes a post 58 projecting perpendicular thereto. The first arm 12 has a cylindrical portion 60 corresponding to the shape of the circular plate 56 and having an opening 62 in the bottom surface thereof for receiving the post 58 therethrough, as shown in FIG. 7. The interconnection of the post 58 of the second arm 14 within the opening 62 of the first arm 12 allows the first and second arms 12, 14 to articulate with respect to one another, specifically by allowing for pivoting about the axis of the post 58. In order to rotationally secure the first and second arms 12, 14 together, a bushing 64 may be secured (e.g., press fit) onto the post 58 after it has been received through the opening 62, so as to prevent the post 58 from withdrawing from the opening 62 while allowing for pivoting between those components.

In order to accommodate flow of the hydraulic fluid through the hinge portion 16 between the first arm 12 and the second arm 14, the post 58 may be hollow, so as to communicate with the interior of the cylinder 50. Additionally, to allow for pivoting about the post 58 while preventing hydraulic fluid from escaping at its interface with the opening 62, a seal member, which may be in the form of an o-ring 47-c, may be provided at that interface, such as by positioning the seal member around the post 58 between the bottom surface of the first arm 12 and the bushing 64.

Figure 6:
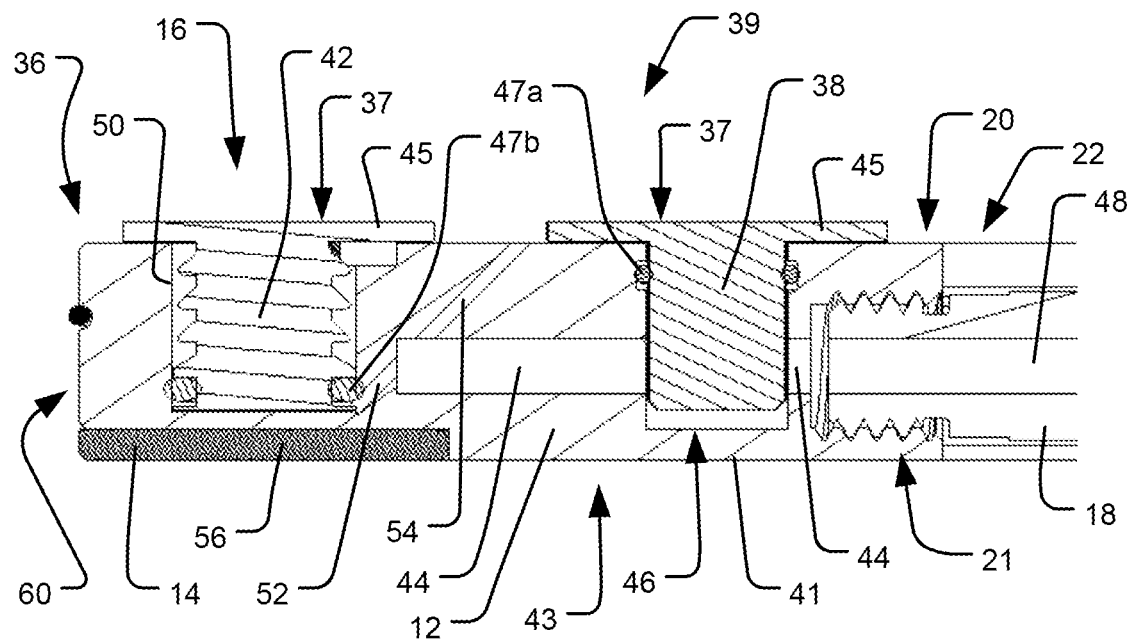
FIG. 6 is a side cross-sectional view of the spinal implant of FIG. 1 connected to the delivery tool, taken along line 6-6 of FIG. 2B.

The hollow post 58 in the second arm 14 may communicate with a channel 66 in the second arm 14 that also communicates with the cylinder 68 within which the second piston 40 is disposed, so that the hydraulic fluid may also drive the outward expansion of the second piston 40. The channel 66 may be formed by drilling a bore along the second arm 14 from the proximal end 20 of the implant 10. If formed in that manner, the extraneous end 67 of the channel 66 may subsequently be plugged, so that the hydraulic fluid does not escape the implant 10 via that path. So that the piston 40 can slide with respect to the cylinder 68 without allowing hydraulic fluid to escape at that interface, a seal member, which may be in the form of an o-ring 47d, may be provided between the second piston 40 and the associated cylinder 68 in the same manner as illustrated in FIG. 6 with respect to the first piston 38 and associated cylinder 46.

The implant 10 may include a locking system to lock the positions of the pistons, at least by preventing them from retracting back into the cylinders once expanded. For example, the pistons may include ratcheting components that allow the pistons to move in the expansion direction, but automatically resist retraction of the pistons in the opposite direction. Such ratcheting components may also be selectively unlockable, in order to allow the pistons to retract when desired. One embodiment of such ratcheting components is shown in the embodiment of the implant illustrated in FIGS. 1-9 and will now be discussed.

As shown in FIG. 9, the first and second pistons 38, 40 each have respective vertical posts 70, 72 received within respective bores 69, 71 in the implant 10. Those bores 69, 71 desirably help constrain the rotational orientation of the associated pistons 38, 40, and they also desirably help guide the expansion of the pistons 38, 40 along a linear path. The posts 70, 72 include ratcheting teeth 74 therealong. Corresponding pawls 76, 77 are located along the exterior of the body to engage the teeth 74, as shown in FIG. 1, so as to permit the pistons 38, 40 to translate outwardly but restrain the pistons 38, 40 from retracting back into their respective cylinders. Those pawls 76, 77 are positioned within corresponding recesses 78, 79 in the outer surface of the implant 10. The pawls 76, 77 are held within the recesses 78, 79 by respective retaining plates 80, 81 affixed to the outer surface of the implant 10. A respective control cable 82, 83 is connected to each of the pawls 76, 77 at respective connecting holes 84, 85, and the control cables 82, 83 extend around the outer surface of the implant 10 within respective grooves 86, 87. The control cables 82, 83 extend to the delivery tool 18, where they can be controlled by the surgeon via the delivery tool 18. Linear compression springs (not shown) are received around the control cables 82, 83 within each recess 78, 79, so as to bias the pawls 76, 77 along the recesses 78, 79 and into engagement with the ratcheting teeth 74. Thus, when the cables 82, 83 are pulled, the respective pawls 76, 77 will slide along the respective recesses 78, 79 away from the vertical posts 70, 72, thus disengaging the pawls form the ratcheting teeth 74 and allowing the pistons 38, 40 to retract back into their respective cylinders. The central piston 42 can similarly be controlled by a corresponding pawl 88 received within a recess 89 in the outer surface of the implant 10 and held there by a retaining plate 90 affixed to the outer surface of the implant. The pawl 88 is biased by a spring (not shown) into engagement with ratcheting teeth 74 on the outer surface of the piston 42, and the pawl 88 can be disengaged from the ratcheting teeth 74 of the piston 42 by the same control cable 82 that controls pawl 76, which control cable 82 connects to the pawl 76 via connecting hole 91. As the control cable 83 that controls pawl 77 extends all the way around the outside of the implant 10, it can pass through holes 92 in pawls 76 and 88 without being secured thereto. The central piston 42 may also include a vertical post 93 received within a bore 94 in the implant 10 to help constrain the rotational orientation of the piston 42 and help guide the expansion of the piston 42 along a linear path.

Figure 10:
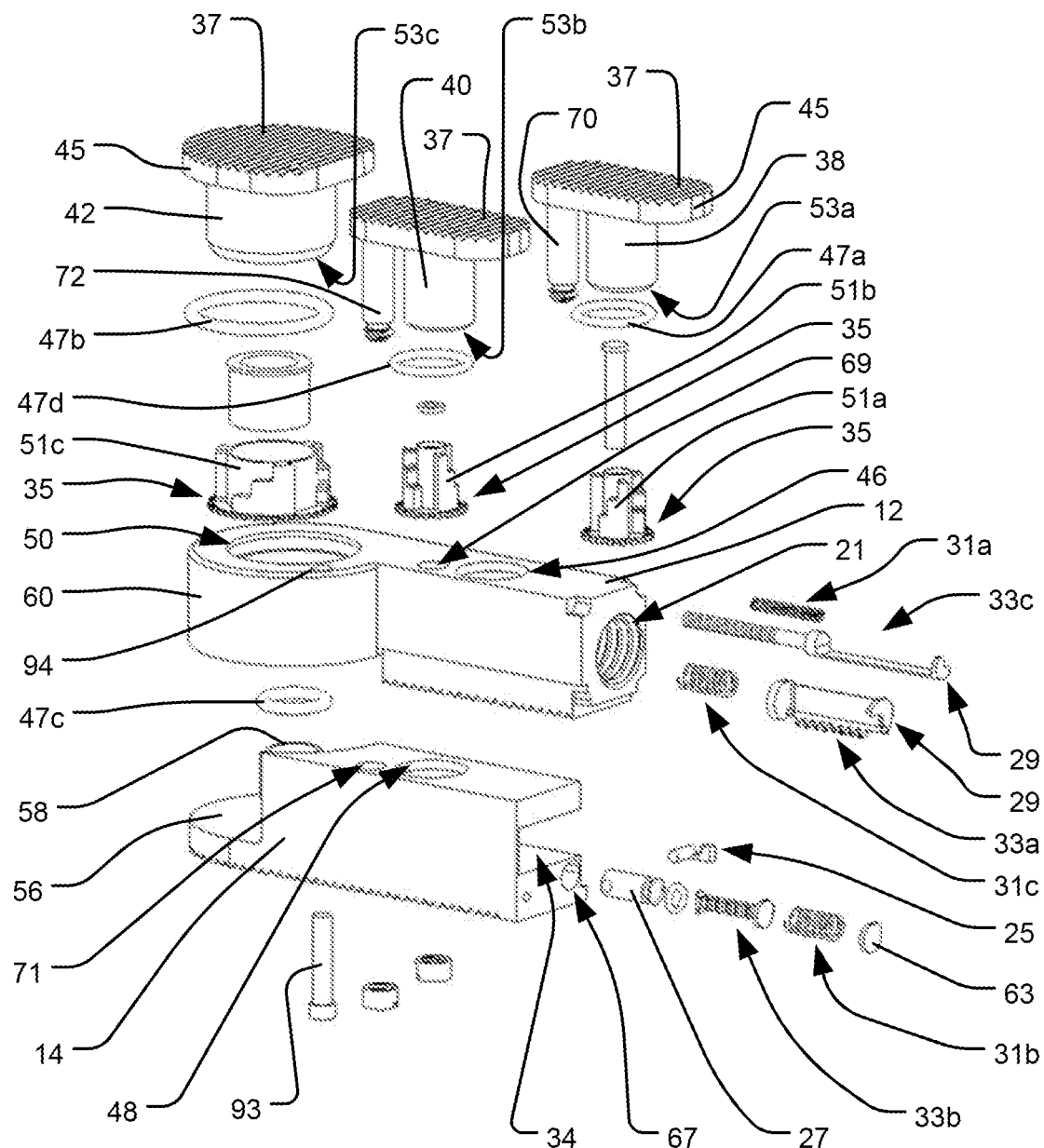
FIG. 10 is an exploded perspective view of a spinal implant in accordance with another embodiment of the present invention.
Figure 11A:
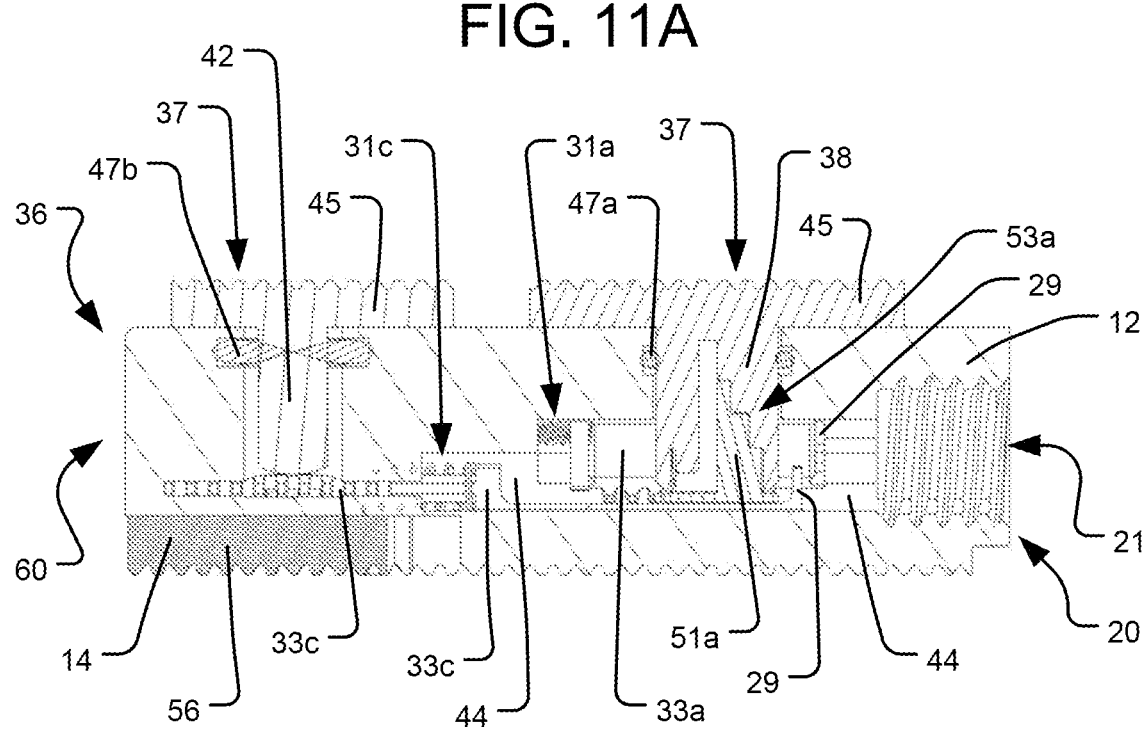
FIG. 11A is a side cross-sectional view of the spinal implant of FIG. 10, taken along the longitudinal axis of the first arm 12.
Figure 11B:
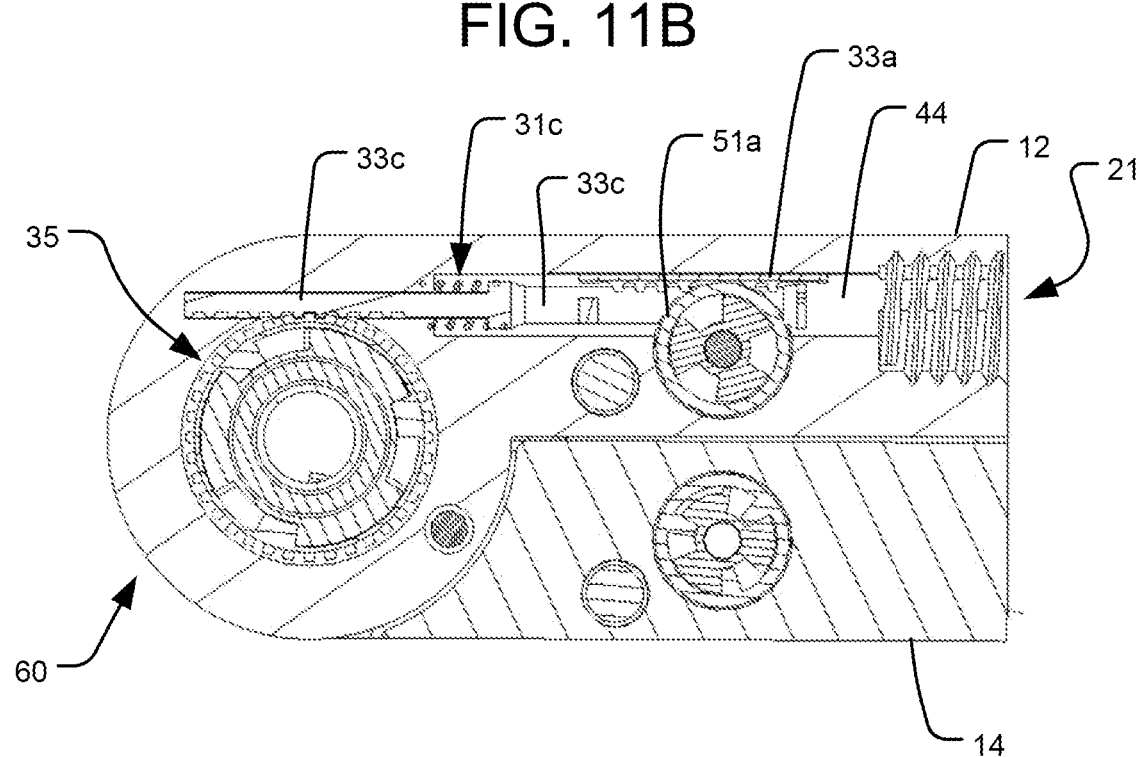
FIG. 11B is a cross-sectional plan view of the spinal implant of FIG. 10, taken along the longitudinal axis of the first arm 12.
Figure 12A:
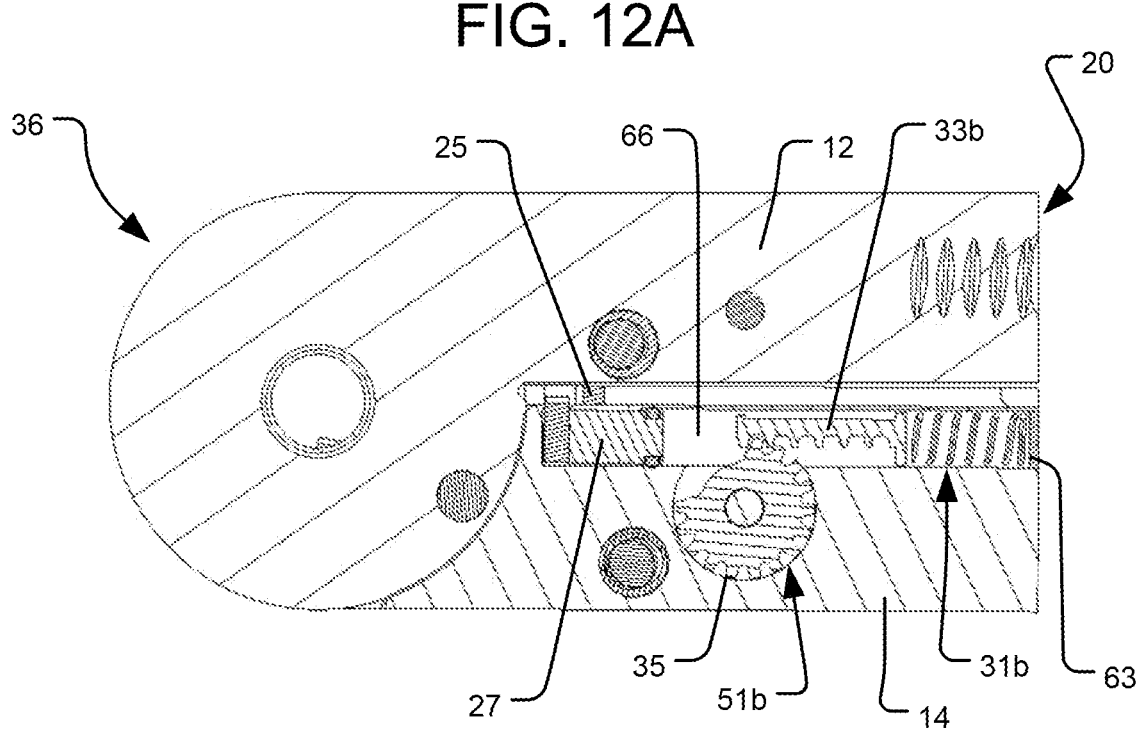
FIG. 12A is cross-sectional plan view of the spinal implant of FIG. 10, taken along the channel 66 in the second arm 14.
Figure 12B:
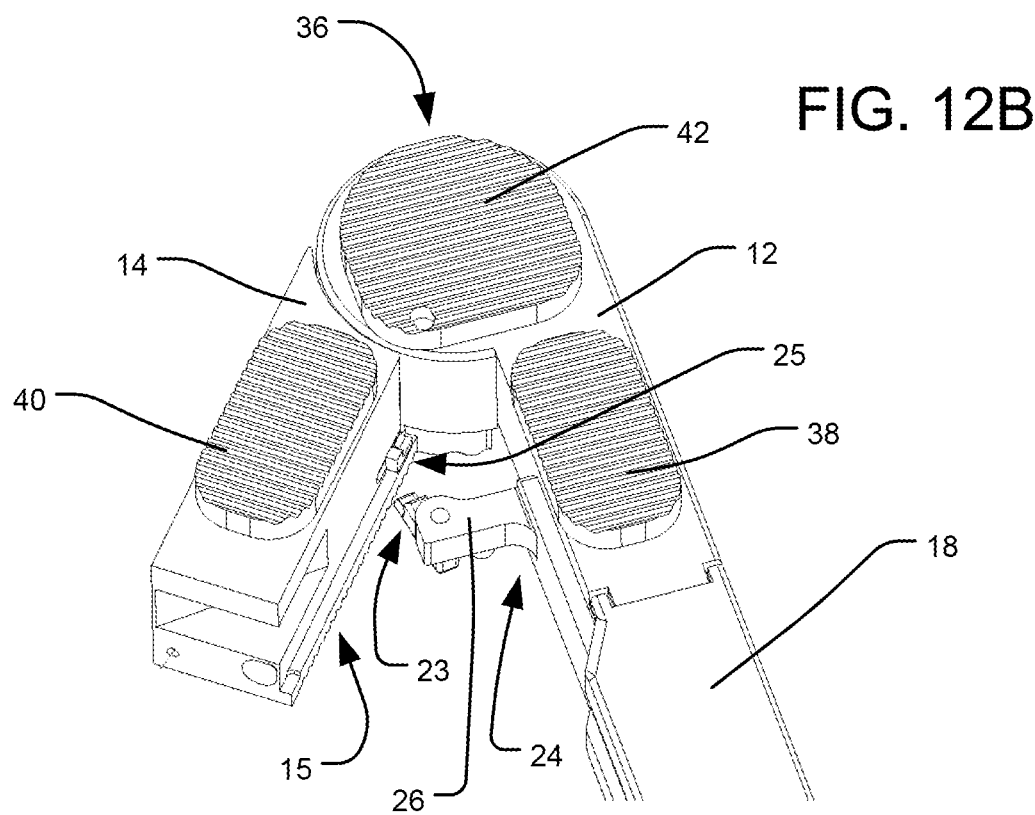
FIG. 12B is a top perspective view of the spinal implant of FIG. 10 in a laterally expanded configuration and connected to the delivery tool.
Figure 12C:
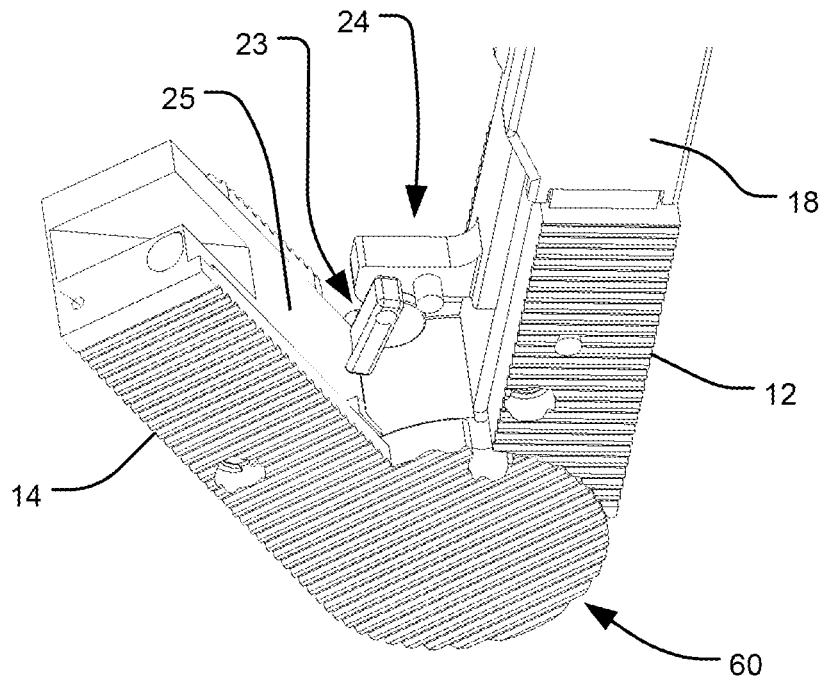
FIG. 12C is a bottom perspective view of the spinal implant of FIG. 10 in a laterally expanded configuration and connected to the delivery tool.
Figure 12D:
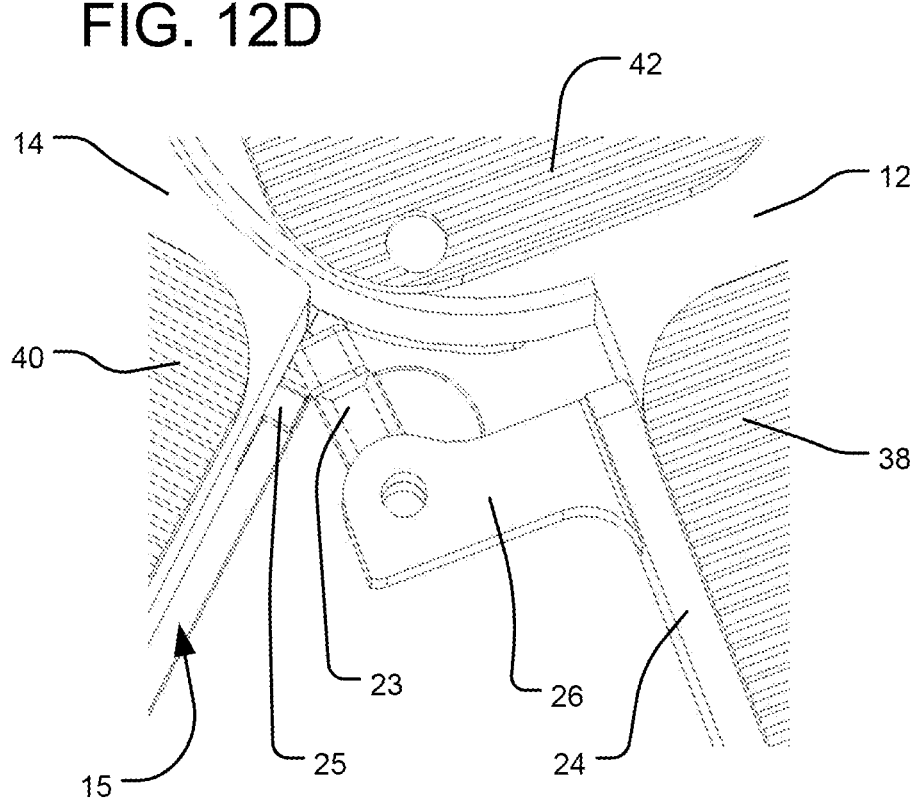
FIG. 12D is an enlarged perspective view of the spinal implant of FIG. 10 in a laterally expanded configuration, with the pivotable arm 23 of the delivery tool in engagement with a pin 25 of the second arm 14.

Other alternative locking systems are possible, however. For example, rotatable, inter-engaging locking elements having tiered, multi-stepped support surfaces, as disclosed in the '620 Patent and the '671 Publication, can be used. That is, as illustrated in FIGS. 10-11, each piston 38, 40, 42 may be connected to a respective upper lock support 53a-c that is structured to releasably engage an associated lower lock support 51a-c. The upper lock supports 53a-c may each resemble an inverted spiral staircase integrally formed inside the respective piston 38, 40, 42, and the lower lock supports 51a-c may each resemble an upright spiral staircase rotatably positioned within the respective cylinder 46, 48, 50. The lower lock supports 51a-c are rotationally biased into mating engagement the upper lock supports 53a-c such that each piston 38, 40, 42 is prevented from retracting back into its respective cylinder 46, 48, 50 at any of a variety of heights when the upper and lower lock supports are engaged. Specifically, as discussed in the '620 Patent and the '671 Publication, the tiered, multi-stepped upper support surfaces of the lower lock supports 51a-c are configured to engage the tiered, multi-stepped lower support surfaces of the upper lock supports 53a-c at any of a variety of levels of expansion, so that the upper lock supports 53a-c (and thus the associated pistons 38, 40, 42) are prevented from translating downwardly.

Each of the lower lock supports 51a-c can be unlocked when desired, by rotating the lower lock supports away from engagement with the corresponding upper lock supports, such that the pistons 38, 40, 42 can retract. In particular, each rotatable lower lock support 51a-c may include gear teeth 35 so as to form a pinion engageable by a corresponding, translatable rack gear 33a-c. Each rack gear 33a-c is biased by a corresponding linear spring 31a-c, which provides the rotational biasing force that drives each of the lower lock supports 51a-c into engagement against the associated upper lock supports 53a-c. The unlocking of any one of the lower lock supports 51a-c may thus include pushing the associated rack gear 33a-c to rotate the lower lock support out of engagement with the upper lock support, which further compresses the associated spring 31a-c. In the first arm 12, lower lock support 51a is engaged by rack gear 33a, and lower lock support 51c is engaged by rack gear 33c. Both of those rack gears 33a, 33c may include engagement plates 29 at their proximal ends, so that the associated lower lock supports 51a, 51c can be unlocked by pushing the engagement plates 29, and thus the rack gears, in the distal direction. The rack gears 33a, 33c may be positioned within the hydraulic channel 44 formed within the first arm 12, such that the engagement plates 29 are accessible via the bore 21, as shown in FIG. 11A. Thus, the delivery tool 18 can include appropriately structured components (not shown) designed to move distally into the bore 21 and push the corresponding rack gears 33a, 33c. The lower lock support 51b in the second arm 14 is engaged by rack gear 33b, such that the lower lock support 51b may be unlocked by moving the rack gear 33b in the proximal direction. That rack gear 33b may be positioned within the hydraulic channel 66 (or some other channel) formed within the second arm 14, and the rack gear 33b may be engaged from the exterior of the second arm 14 to induce the unlocking movement of the rack gear 33b. For example, a piston 27 positioned within the channel 66 and connected to the rack gear 33b may include a pin 25 projecting laterally through a slot along the inner surface 15 of the second arm 14. That pin 25 may be 14 engaged by a tool connected to or associated with the first arm 12. For example, the spreader 24, or a similar component movable distally along the inner side of the first arm 12, may include a pivotable arm 23 for engaging the pin 25. The arm 23 may designed to pivot such that it can slide the pin 25 proximally along the second arm 14, so as to push the rack gear 33b proximally and unlock the lower lock support 51b, as shown in FIGS. 12A-D. That proximal movement of the rack gear 33b results in a further compression of the spring 31b positioned between the rack gear 33b and a plugging cap 63 at the end 67 of the channel 66. In the embodiment illustrated in FIGS. 10-12, the upper and lower lock supports are located inside the respective pistons. However, alternative arrangements in which the lock supports are positioned outside of the respective pistons and at least partially encircle the pistons, as disclosed in the '620 Patent, may also be used.

As discussed above, the pistons 38, 40, 42 may be individually controlled via separate hydraulic pressure channels formed within the implant, or they may be controlled by a single hydraulic pressure channel, as in the embodiment of FIGS. 1-9. One benefit of having all of the pistons 38, 40, 42 controlled with a single hydraulic pressure channel, and thus a single hydraulic pressure input, is that it can result in simplicity of construction and use of the implant 10. Moreover, with a single hydraulic pressure channel, the implant 10 may be designed such that the pistons 38, 40, 42 will apply different forces to the engaged vertebral body at pre-defined ratios to one another. That is, since the pressure within the single hydraulic pressure channel will be uniform, the force applied by any piston will be directly related to the cross-sectional area of that piston, as force equals pressure multiplied by area. Thus, by selecting the cross-sectional area of each of the pistons 38, 40, 42, the ratios of the forces applied by the pistons can be pre-defined. For example, the table below provides some exemplary force ratios based on the diameter of the central piston 42 vis-à-vis the first and second pistons 38, 40 (where the first and second pistons have the same area). It is noted that the force ratios provided in the below table are the ratio of the force applied by the first and second pistons 38, 40 together (i.e., the sum of the force applied by each of those pistons) to the force applied by the central piston 42.

| Diameter of central piston 42 (mm) | Diameter of first and second pistons 38, 40 (mm) | Area of central piston 42 (mm²) | Area of first and second pistons 38, 40 (mm²) | Force ratio (first and second pistons 38, 40:central piston 42) |
|---|---|---|---|---|
| 5 | 3 | 314.16 | 113.10 | 0.72 |
| 6 | 3 | 452.39 | 113.10 | 0.50 |
| 7 | 3 | 615.75 | 113.10 | 0.37 |
| 5 | 4 | 314.16 | 201.06 | 1.28 |
| 6 | 4 | 452.39 | 201.06 | 0.89 |
| 7 | 4 | 615.75 | 201.06 | 0.65 |
| 5 | 5 | 314.16 | 314.16 | 2.00 |
| 6 | 5 | 452.39 | 314.16 | 1.39 |
| 7 | 5 | 615.75 | 314.16 | 1.02 |
| 9 | 3 | 1017.88 | 113.10 | 0.22 |
| 9 | 4.5 | 1017.88 | 254.47 | 0.5 |
| 9 | 6 | 1017.88 | 452.39 | 0.89 |
| 7.6 | 3 | 725.83 | 113.10 | 0.31 |
| 7.6 | 4 | 725.83 | 201.06 | 0.55 |
| 7.6 | 5 | 725.83 | 314.16 | 0.87 |

Desirably, by applying different forces at different locations along the implant 10, the implant can create different amounts of expansion at those different locations. Beneficially, such differential expansion can be used for lordosis correction. For example, the nerve roots can be decompressed by providing some expansion at the posterior portion of the spine, and lordosis can be corrected by providing a greater amount of expansion at the anterior portion of the spine.

Figure 13:
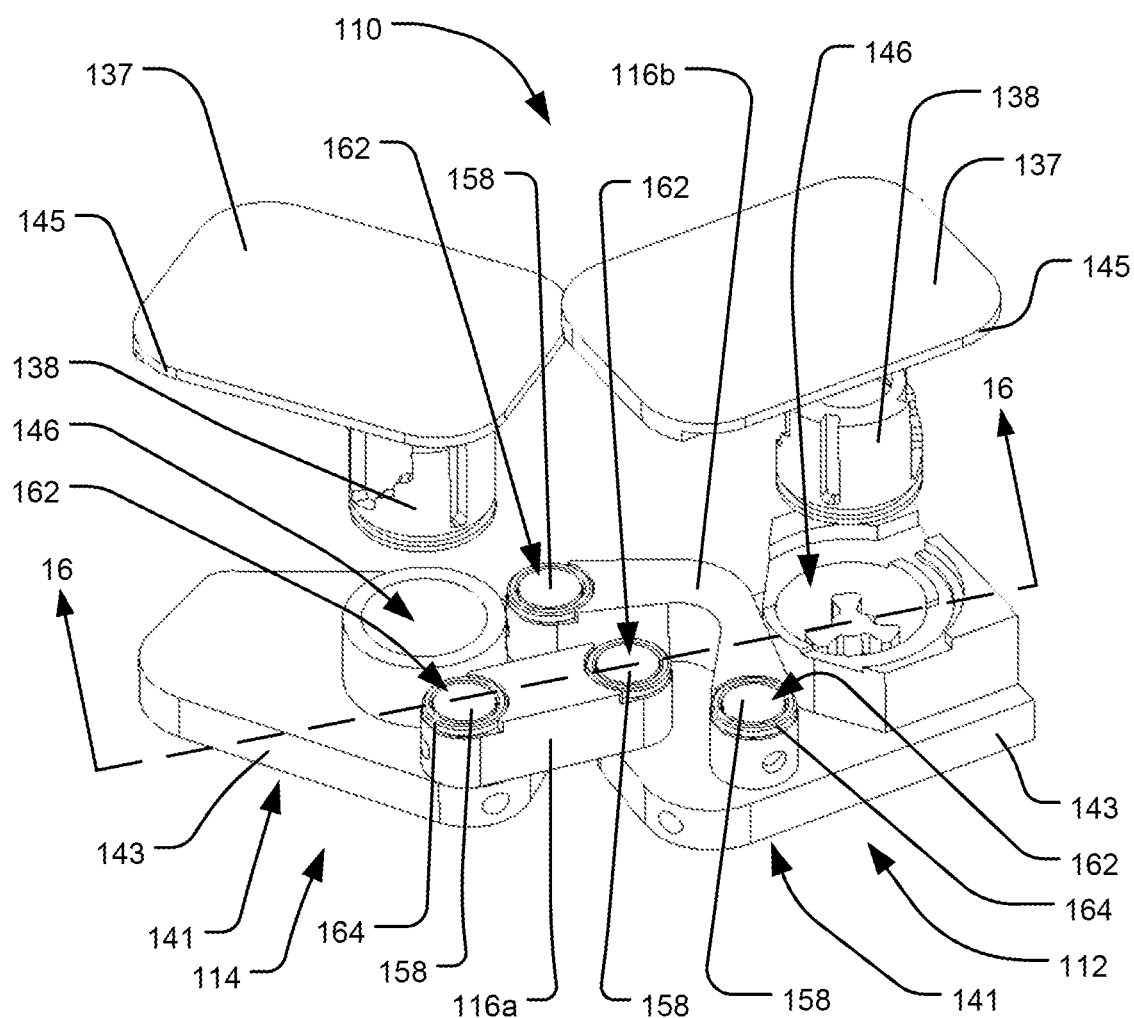
FIG. 13 is a partially exploded perspective view of a spinal implant in accordance with another embodiment of the present invention.
Figure 14:
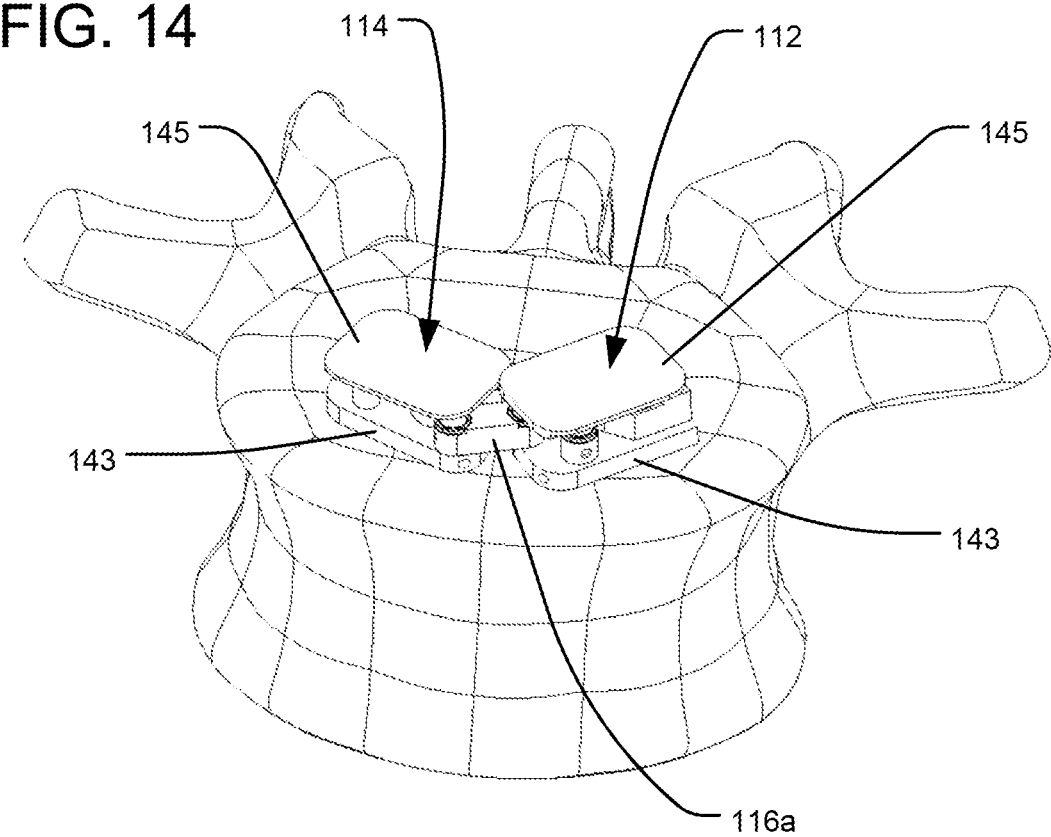
FIG. 14 is a perspective view of the spinal implant of FIG. 13 positioned in an intervertebral space.
Figure 15:
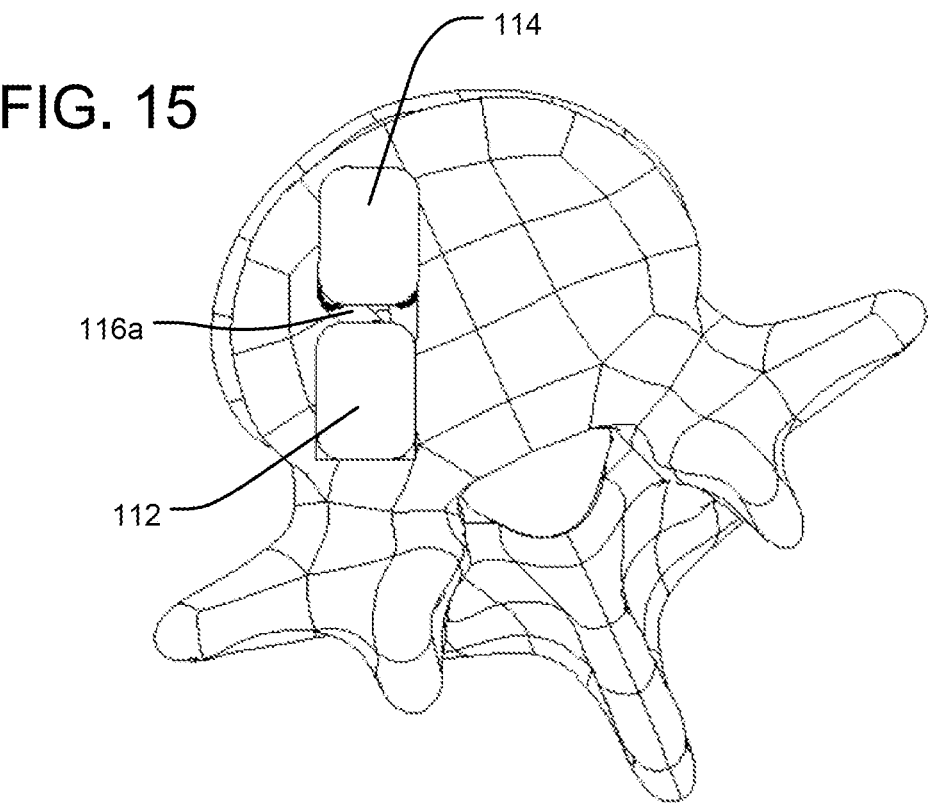
FIG. 15 is a top plan view of the spinal implant of FIG. 13 during insertion into the intervertebral space.

Another embodiment of an implant 110 having a first segment 112 and second segment 114 in accordance with the present invention is illustrated in FIGS. 13-16. In that embodiment, rather than the two segments 112, 114 of the implant 110 being in the form of long and narrow first and second arms, as shown in the above-discussed figures of the previous embodiments, the two segments 112, 114 may be shorter and wider (and they may also be closer to squares). Moreover, rather than being directly connectable together at a pivot axis, the segments 112, 114 may be somewhat spaced apart and connected together by one or more linkages 116. The linkages are desirably rigid links pivotably connected to each segment 112, 114 at their opposite ends. That is, each linkage 116 may have a cylindrical opening 162 at each end sized to receive a respective post 158 connected to each of the segments 112, 114 (e.g., connected to the bottom plates 143), so that the linkages 116 are pivotable about the posts 158. Moreover, bushings 164 may be secured (e.g., press fit) onto the posts 158 after they have been received through the openings 162, so as to prevent the posts 158 from withdrawing from the openings 162 while allowing for pivoting between those components. As shown in FIG. 13, one of the linkages 116a may be a straight link 116a connecting the left proximal corner of the second segment 114 to a distal end of the first segment 112, either centrally located in the left/right direction or towards the right side of the first segment 112. Another linkage 116b may connect the right proximal corner of the second segment 114 to a left side of the first segment 112, proximally of the distal end. That second linkage 116b may have a bent profile (e.g., with a 90° bend), so as to avoid interference with the first linkage 116a. In other alternative embodiments, straight linkages (such as those illustrated in the embodiment of FIGS. 17-22), crossing linkages (not shown), or other suitable linkage arrangements may be used.

Each segment 112, 114 of the implant 110 may comprise a top plate 145 having an upper vertebral engaging surface 137 and a bottom plate 143 having a lower vertebral engaging surface 41. Hydraulically driven pistons 138 received in corresponding cylinders 146, similar to those discussed above, can be positioned between the top and bottom plates 145, 143 for driving them apart. The segments 112, 114 may also include any appropriate locking system for automatically preventing the top and bottom plates 145, 143 from retracting back towards one another, except when deliberately unlocked by the user. For example, each segment 112, 114 may have a respective locking element that may take the form of any of the locking elements discussed above or those disclosed in the '620 Patent or the '671 Publication. Alternatively, the locking elements may take the form of those discussed below in connection with FIGS. 23-29.

Figure 16:
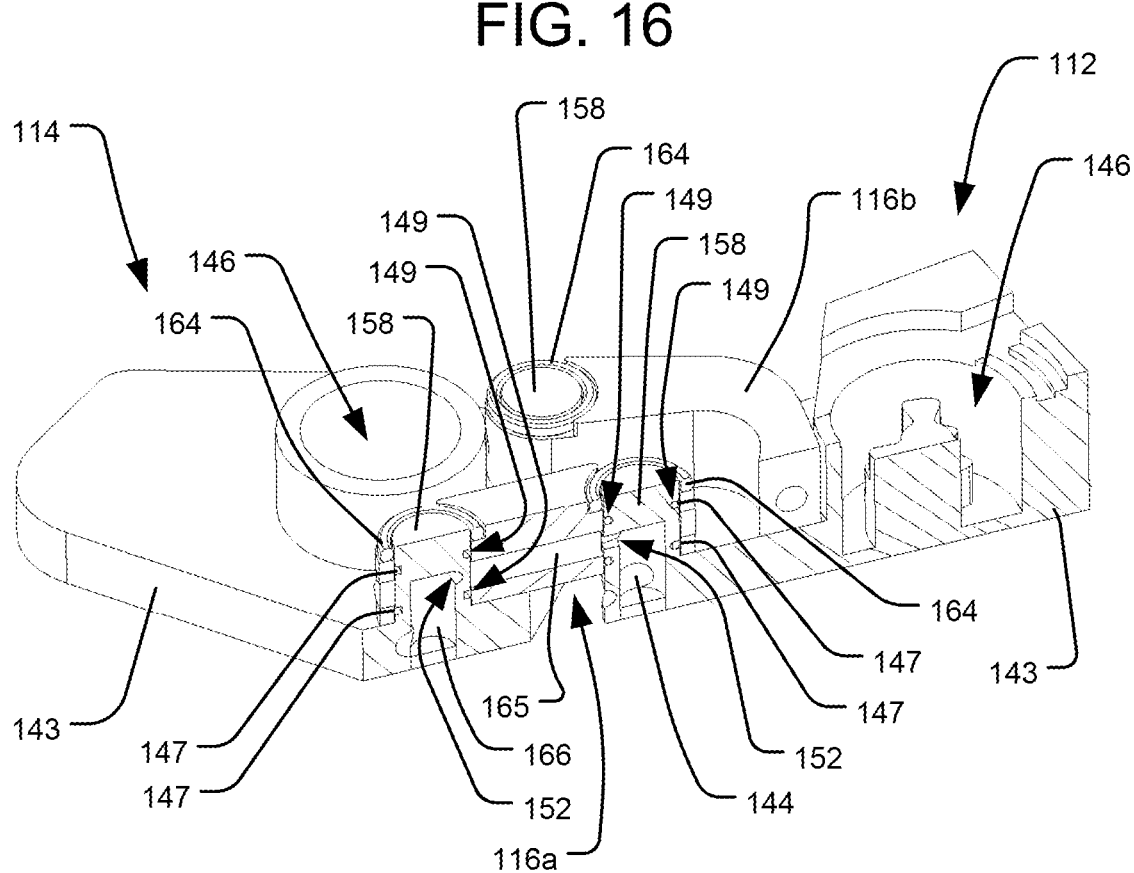
FIG. 16 is a perspective cross-sectional view of the spinal implant of FIG. 13, taken along line 16-16.
Figure 17:
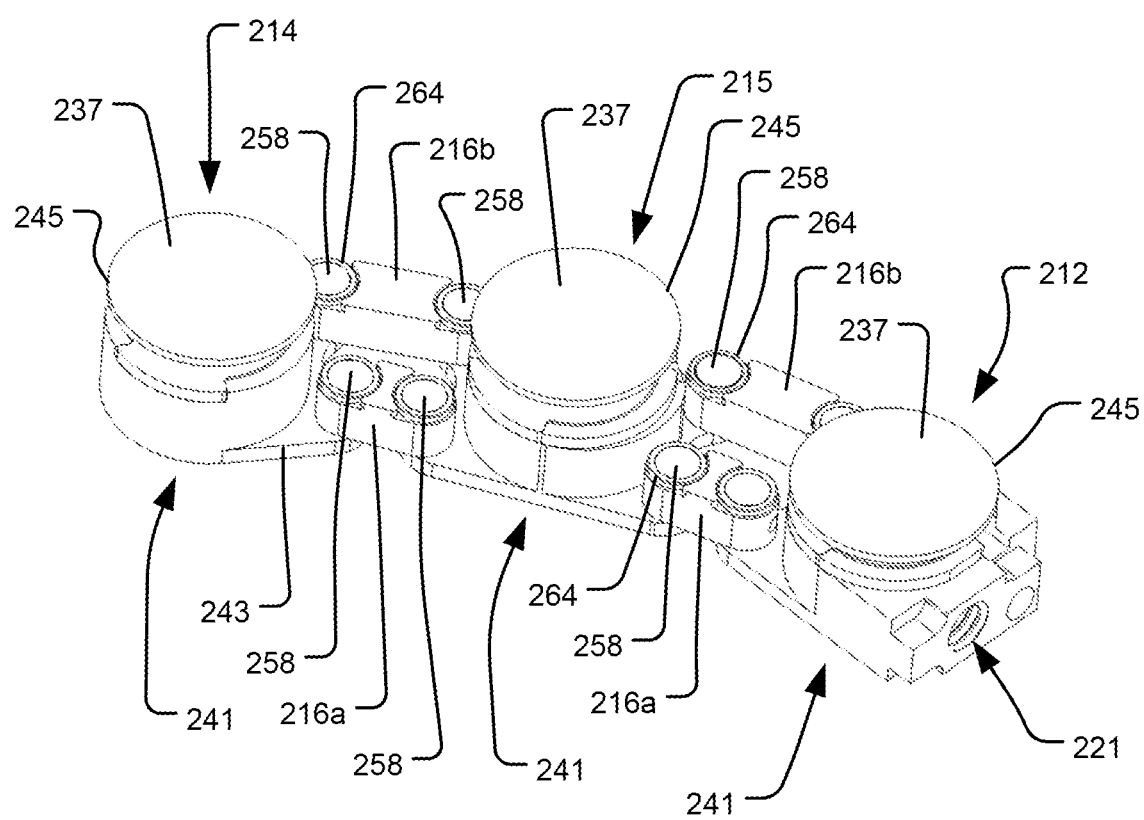
FIG. 17 is a perspective view of a spinal implant in accordance with another embodiment of the present invention.

Either or both of the linkages 116a, 116b connecting the first and second segments 112, 114 of the implant 110 may be configured to transmit the hydraulic fluid therethrough, so that a single hydraulic pressure channel may be common to the expansion mechanisms (e.g., pistons/cylinders) of both segments 112, 114. That is, as discussed above, the cylinders 146 within which the pistons 138 are disposed may be interconnected by a series of channels, which may be formed in the bottom plate 143. Those channels formed in the first segment 112 may communicate with one or both posts 158 of the first segment 112. For example, as shown in FIG. 16, the posts 158 of the first segment 112 may be hollow so as to define a fluid channel 144 therein. The linkages 116a, 116b may similarly be hollow so as to define a fluid channel 165 therein. Finally, the posts 158 of the second segment 114 may also be hollow so as to define a fluid channel 166 therein, which channel 166 may communicate either directly or indirectly with the cylinder of the second segment 112. In order for the hydraulic fluid to flow between the fluid channels 144, 166 of the posts 158 and the fluid channels 165 of the linkages 116a, 116b, slots 152 may be provided in each of the posts 158. Moreover, seal members, which may be in the form of o-rings 147, may be positioned in corresponding grooves 149 of the posts 158, both above and below the slots 152, so as to seal the network of fluid channels defined within the linkages 116 while allowing the linkages to pivot.

Desirably, the linkages 116 of the implant 110 may be configured so as to allow the first and second segments 112, 114 to be aligned in a collinear arrangement, as shown in FIG. 13. That way, the implant 110 may beneficially take up a small area in the lateral direction during insertion, after which the implant may be articulated within the intervertebral space to achieve a final configuration like that illustrated in FIG. 12, which may be towards the anterior portion of the spine. Although the embodiment of the implant 10 discussed above in connection with FIGS. 1-9 was shown being inserted with hinge portion 16 leading and the first and second arms 12, 14 trailing, it is noted that the first and second arms 12, 14 of that embodiment could also be implanted in a collinear arrangement similar to that shown in FIG. 15. Specifically, the arms 12, 14 of that implant 10 may initially be spread apart such that they are positioned on opposite sides of the hinge portion 16.

Another embodiment of an implant 210 in accordance with the present invention and illustrated in FIGS. 17-29 may be similar to the implant 110 illustrated in FIGS. 13-16, but the implant 210 of FIGS. 17-29 may have three articulating segments 212, 214, 215. Reference numerals in FIGS. 17-29 similar to those used in the embodiment of FIGS. 13-16 refer to analogous elements, and thus such analogous elements may not be separately discussed below in connection with implant 210 of FIGS. 17-29.

Figure 18:
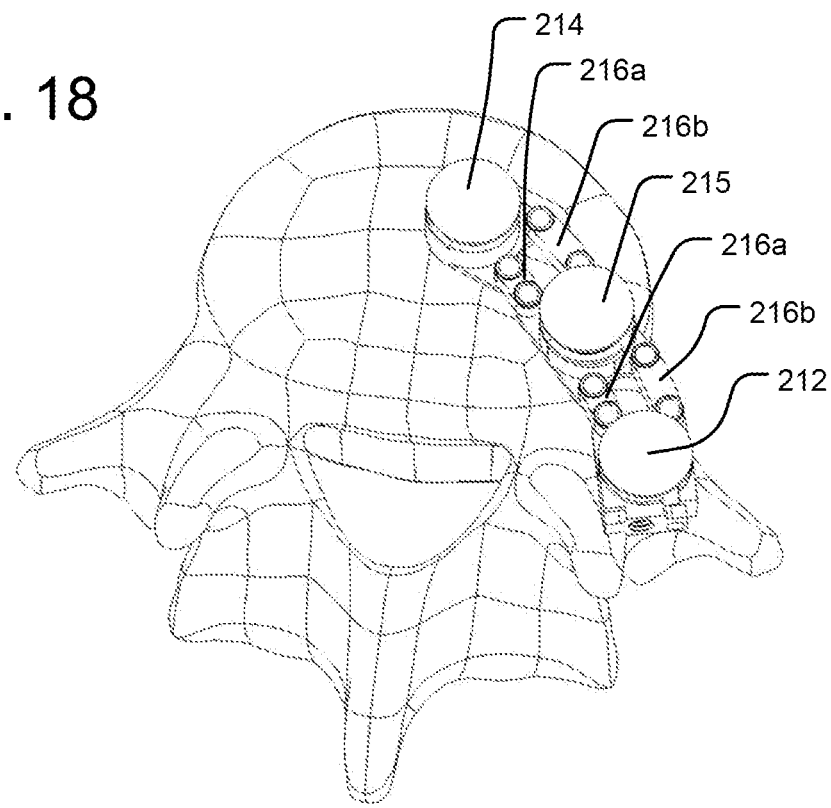
FIG. 18 is a top perspective view of the spinal implant of FIG. 17 during insertion into an intervertebral space.
Figure 19:
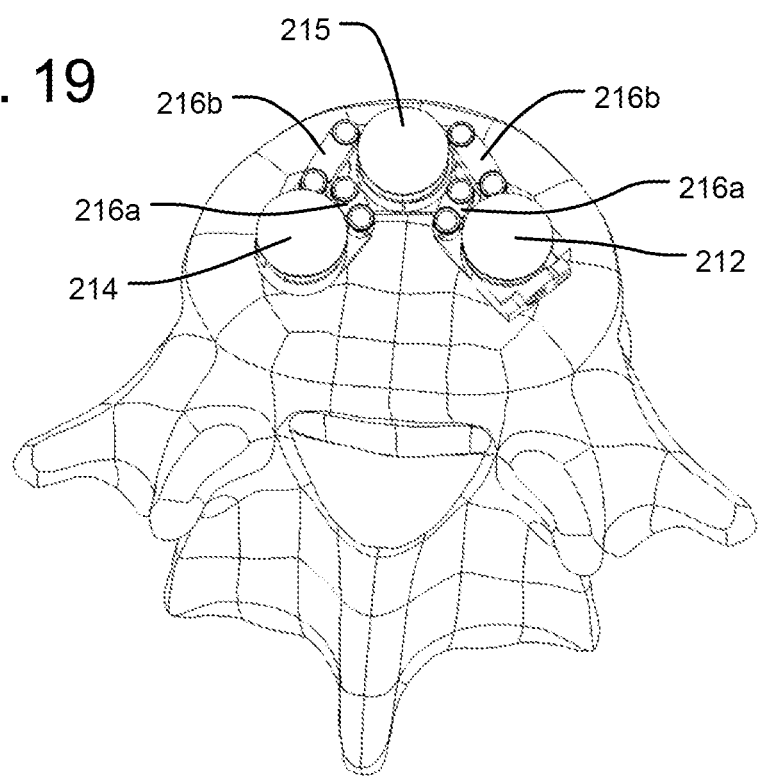
FIG. 19 is a top perspective view of the spinal implant of FIG. 17 positioned in an intervertebral space.
Figure 20:
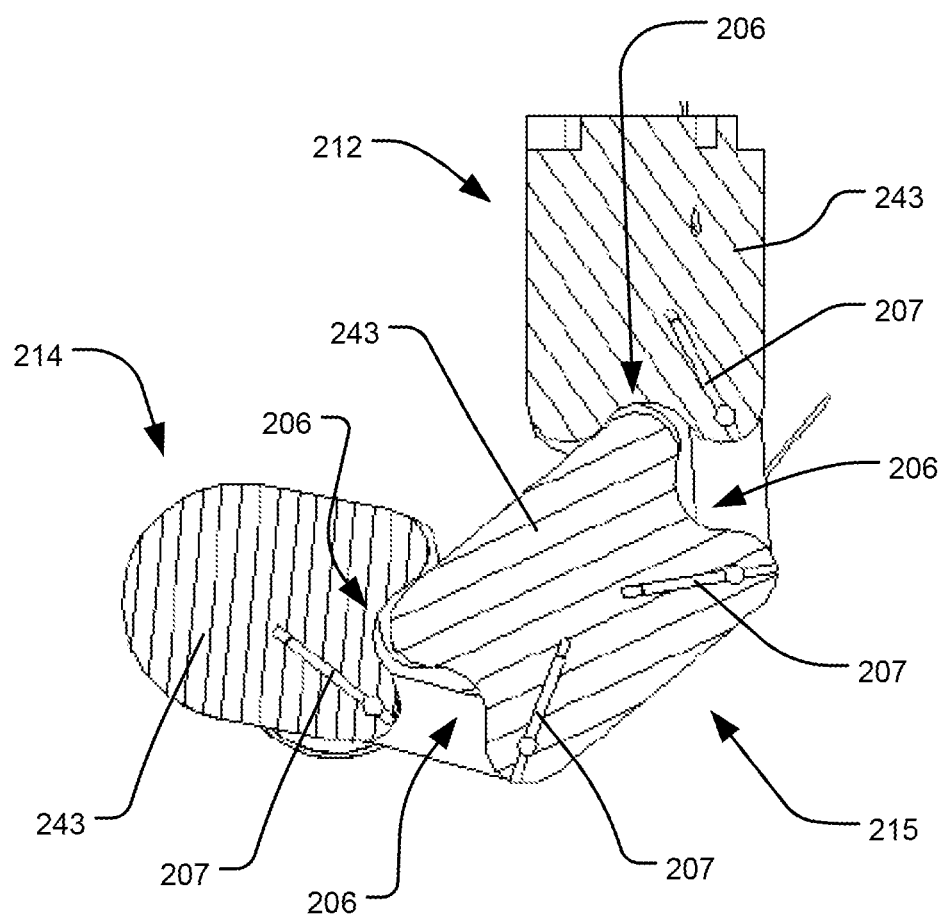
FIG. 20 is a cross-sectional bottom plan view of the spinal implant of FIG. 19 taken along the bottom plates 243 of the implant.
Figure 21A:
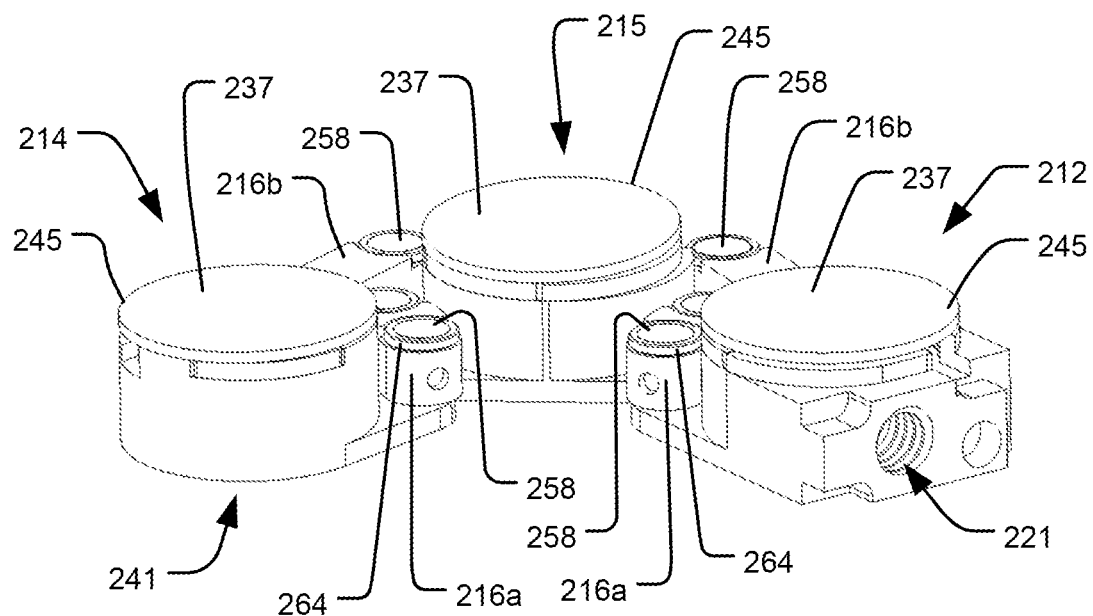
FIG. 21A is a perspective view of the spinal implant of FIG. 17 in a longitudinally contracted configuration.
Figure 21B:
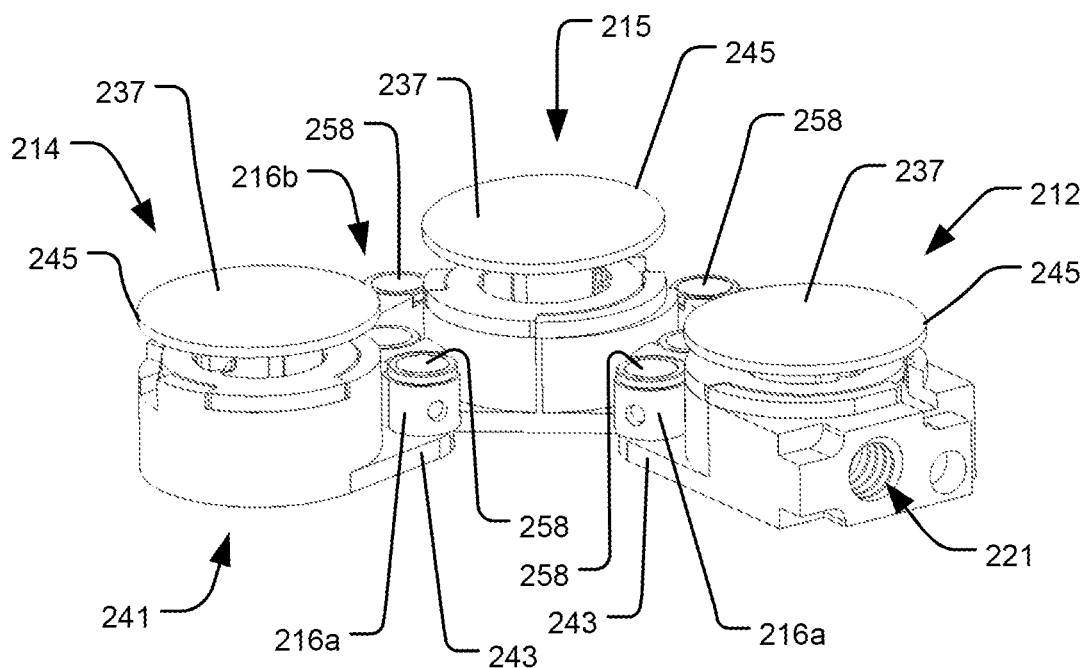
FIG. 21B is a perspective view of the spinal implant of FIG. 17 in a longitudinally expanded configuration.
Figure 22A:
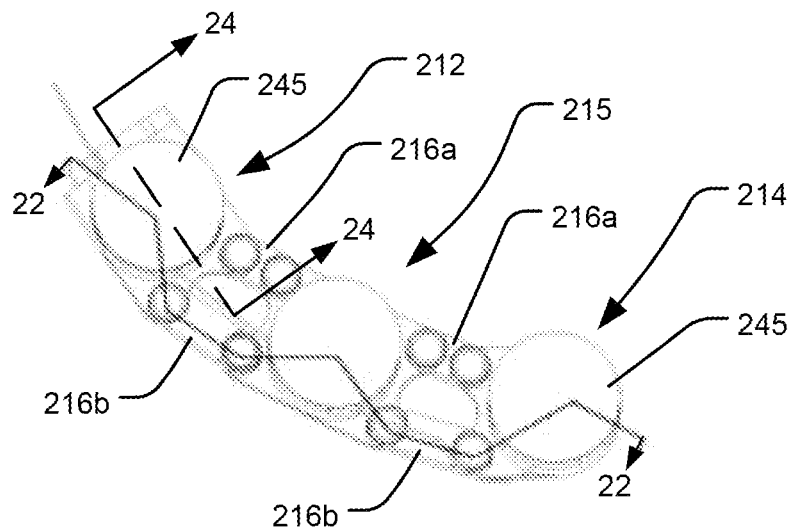
FIG. 22A is a top plan view of the spinal implant of FIG. 17.
Figure 22B:
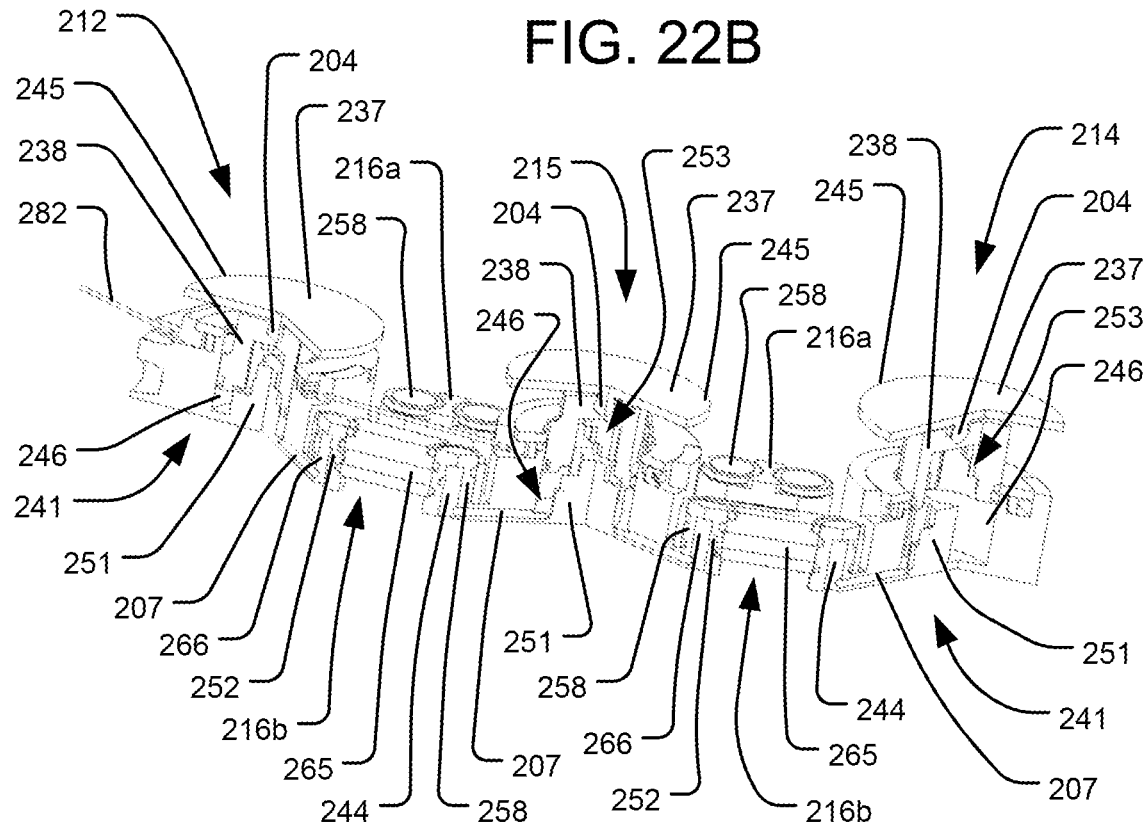
FIG. 22B is a side cross-sectional view of the spinal implant of FIG. 22A taken along line 22-22.
Figure 23:
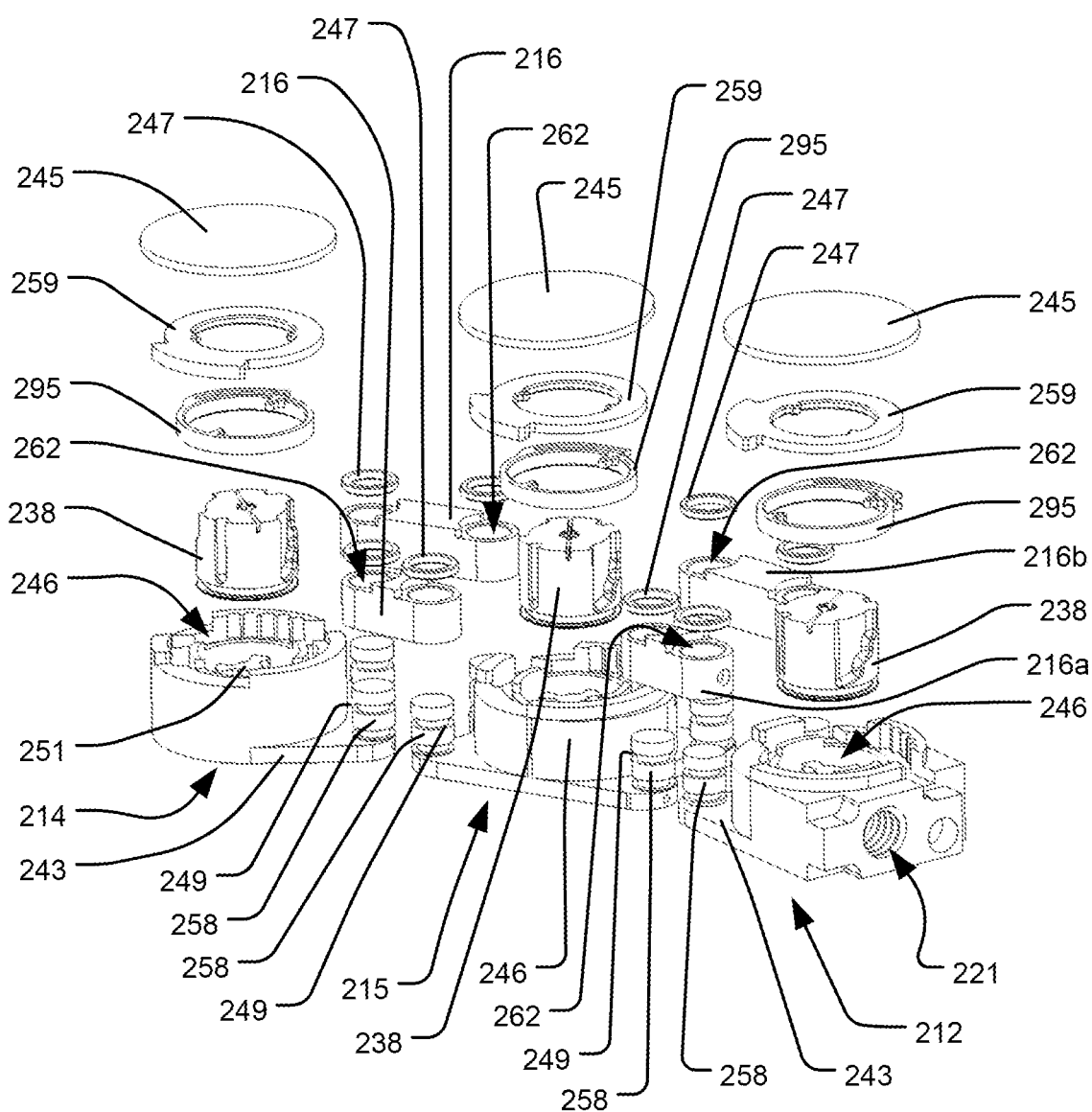
FIG. 23 is an exploded view of the spinal implant of FIG. 17.
Figure 24:
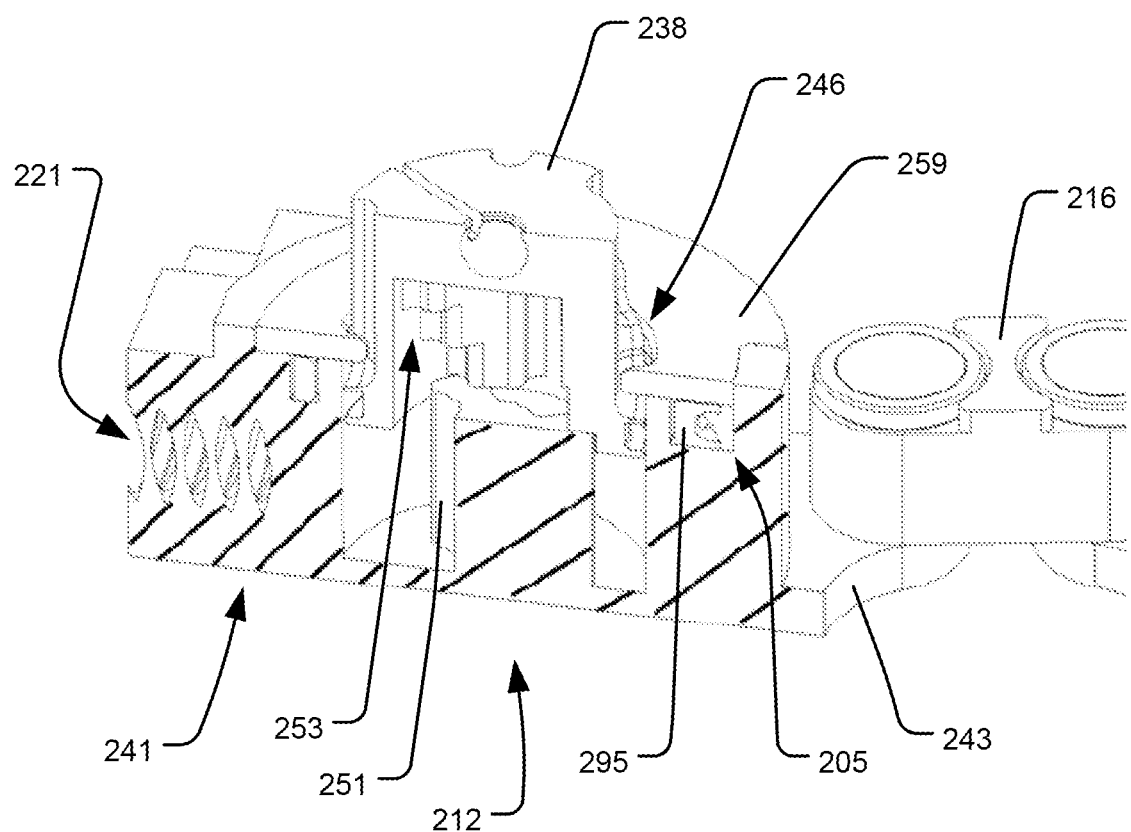
FIG. 24 is a partial, perspective side cross-sectional view of the spinal implant of FIG. 22A taken along line 24-24, with the top plate 245 omitted.
Figure 25A:
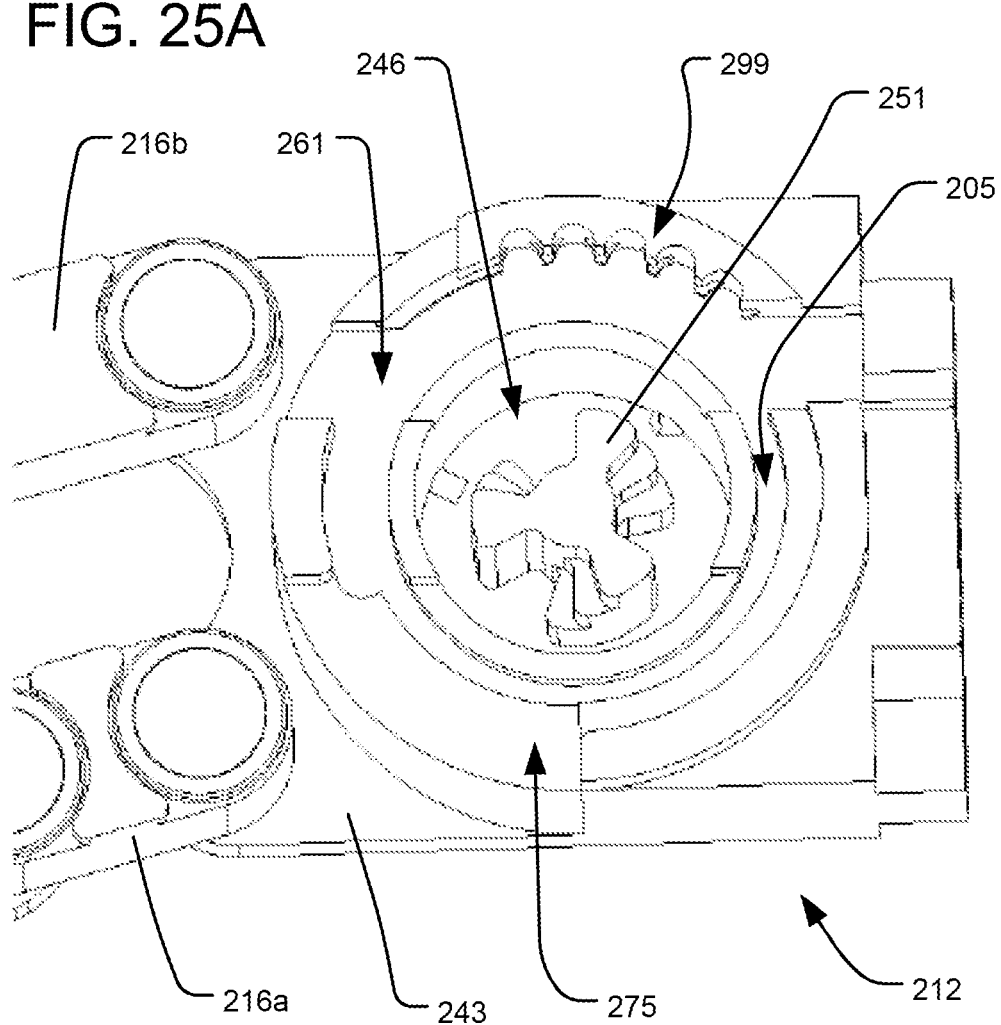
FIG. 25A is a partial top perspective view of one segment 212 of the spinal implant of FIG. 17 with the piston, cam ring, and ratcheting ring omitted.
Figure 25B:
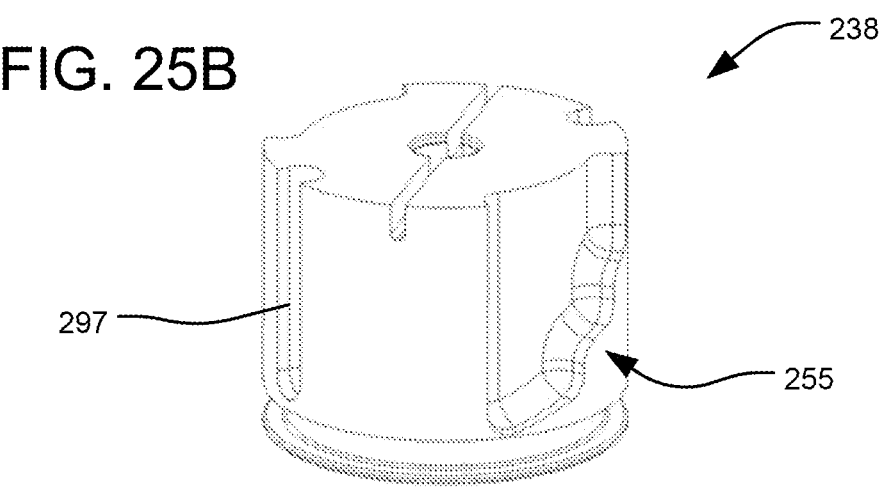
FIG. 25B is a perspective view of a piston of the spinal implant of FIG. 17.
Figure 25C:
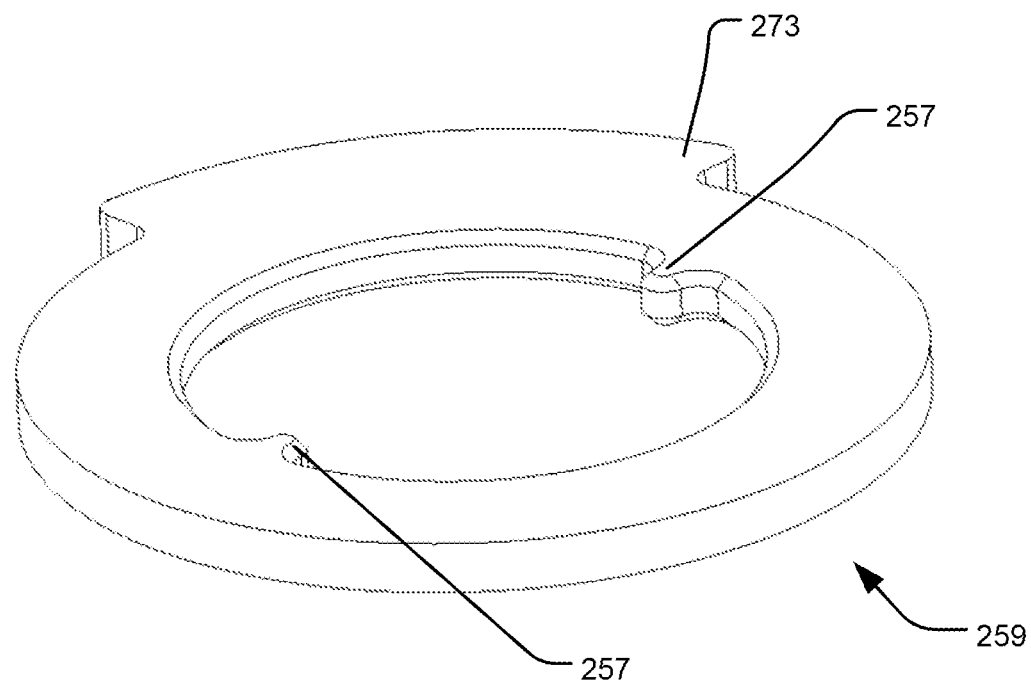
FIG. 25C is a perspective view of a cam ring of the spinal implant of FIG. 17.
Figure 25D:
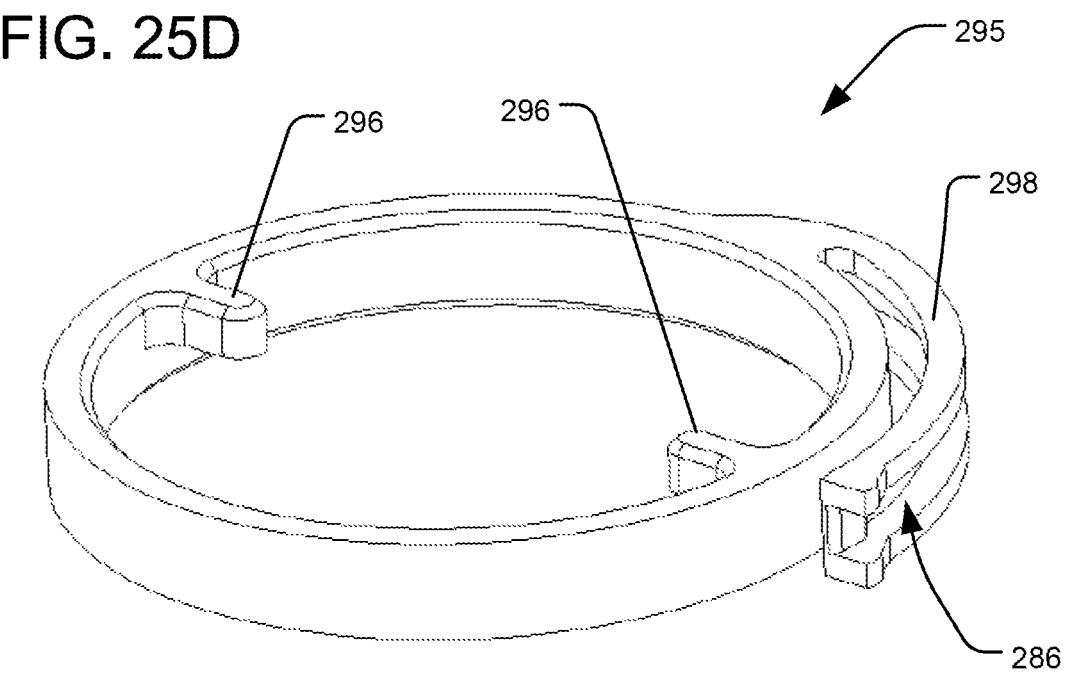
FIG. 25D is a perspective view of a ratcheting ring of the spinal implant of FIG. 17.
Figure 26:
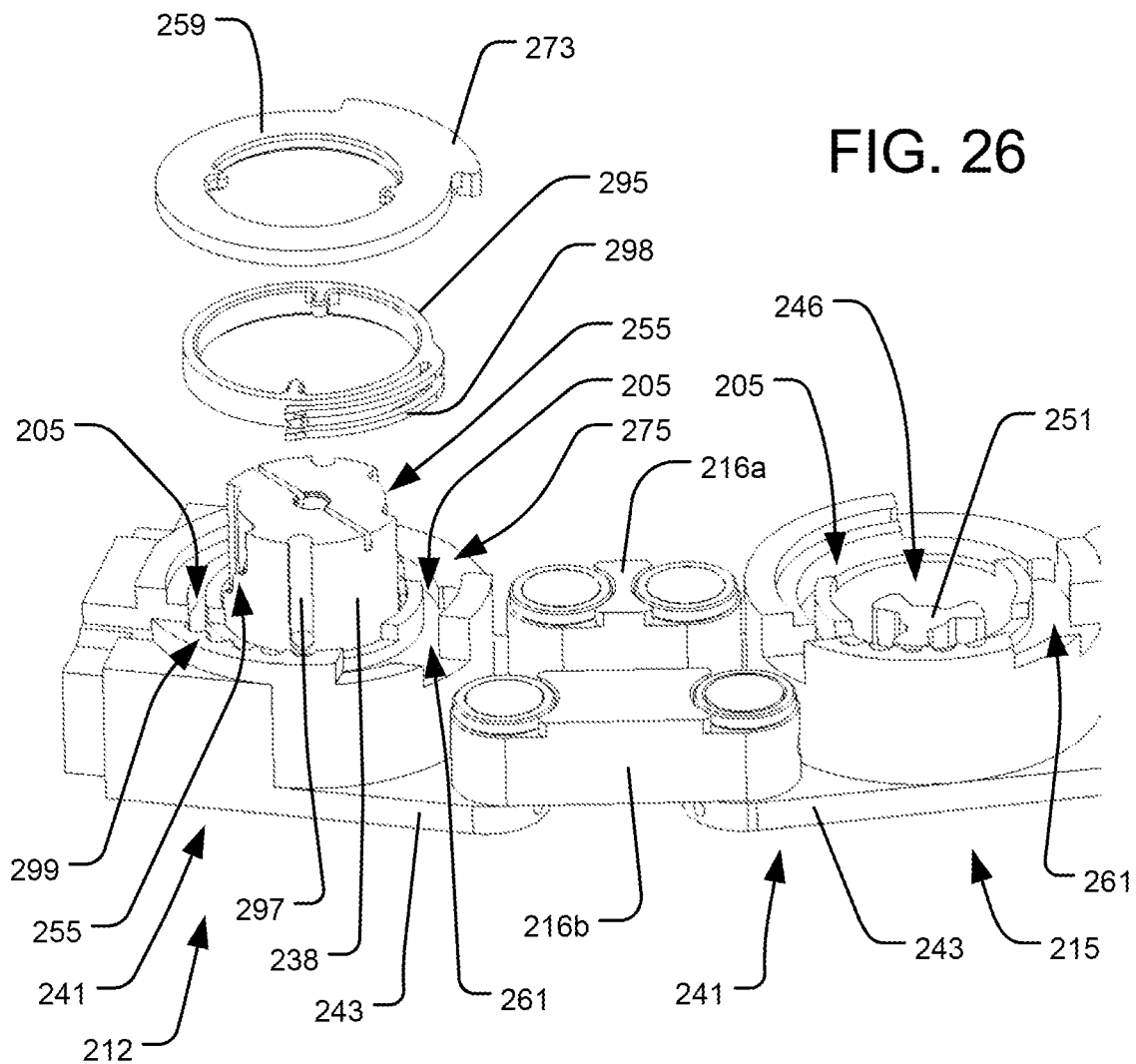
FIG. 26 is a partial, exploded perspective view of the spinal implant of FIG. 17, with the top plate 245 omitted.
Figure 27A:
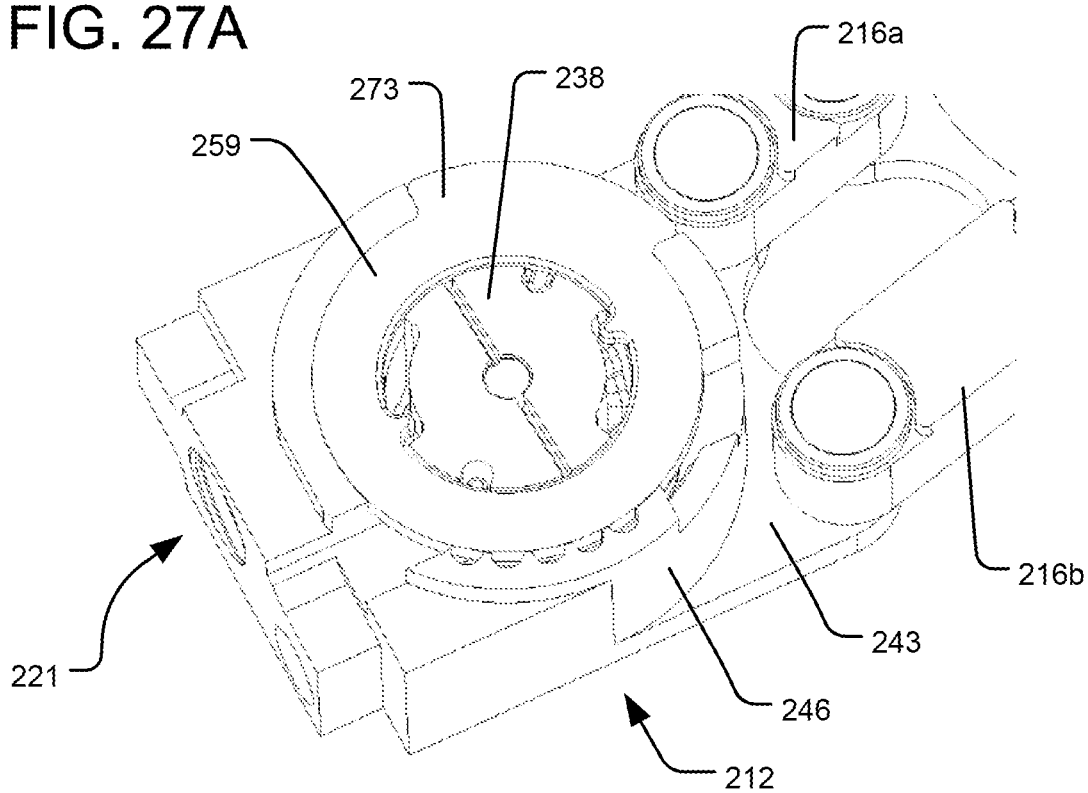
FIG. 27A is a partial perspective view of the spinal implant of FIG. 17, with the top plate 245 omitted, in longitudinally contracted configuration.
Figure 27B:
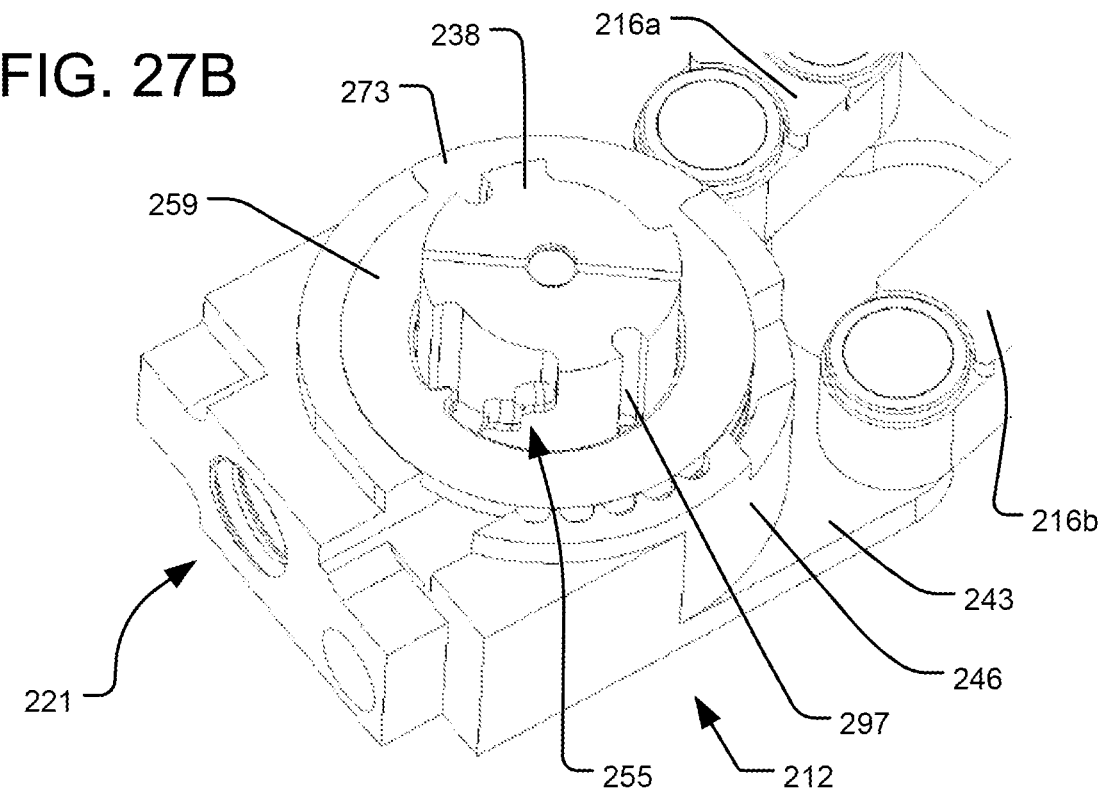
FIG. 27B is a partial perspective view of the spinal implant of FIG. 17, with the top plate 245 omitted, in a longitudinally expanded configuration.
Figure 28A:
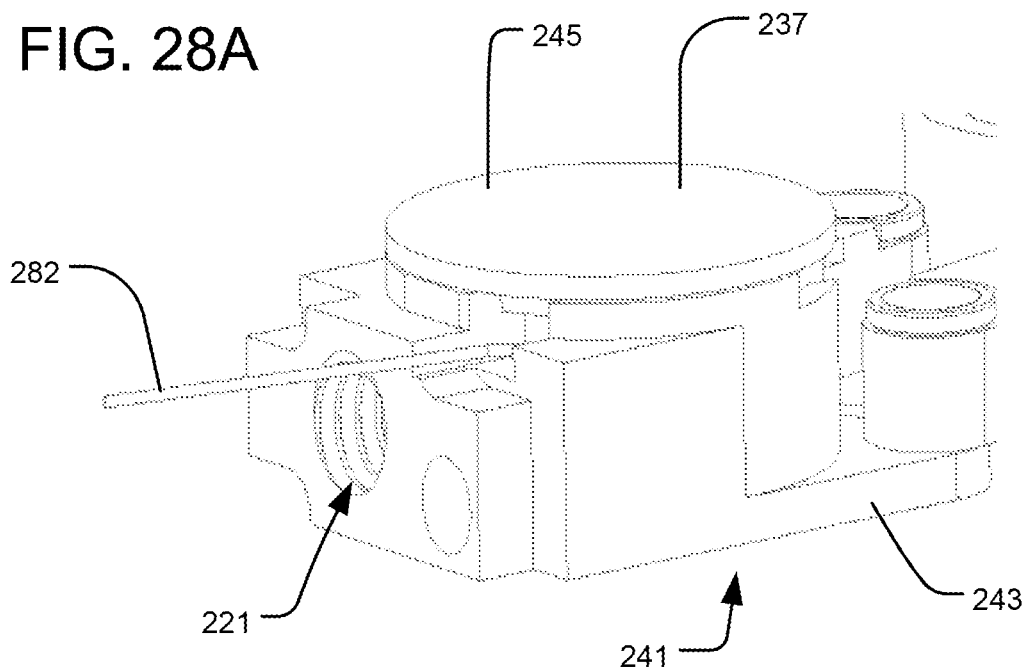
FIG. 28A is partial perspective view of the spinal implant of FIG. 17 in a longitudinally contracted configuration.
Figure 28B:
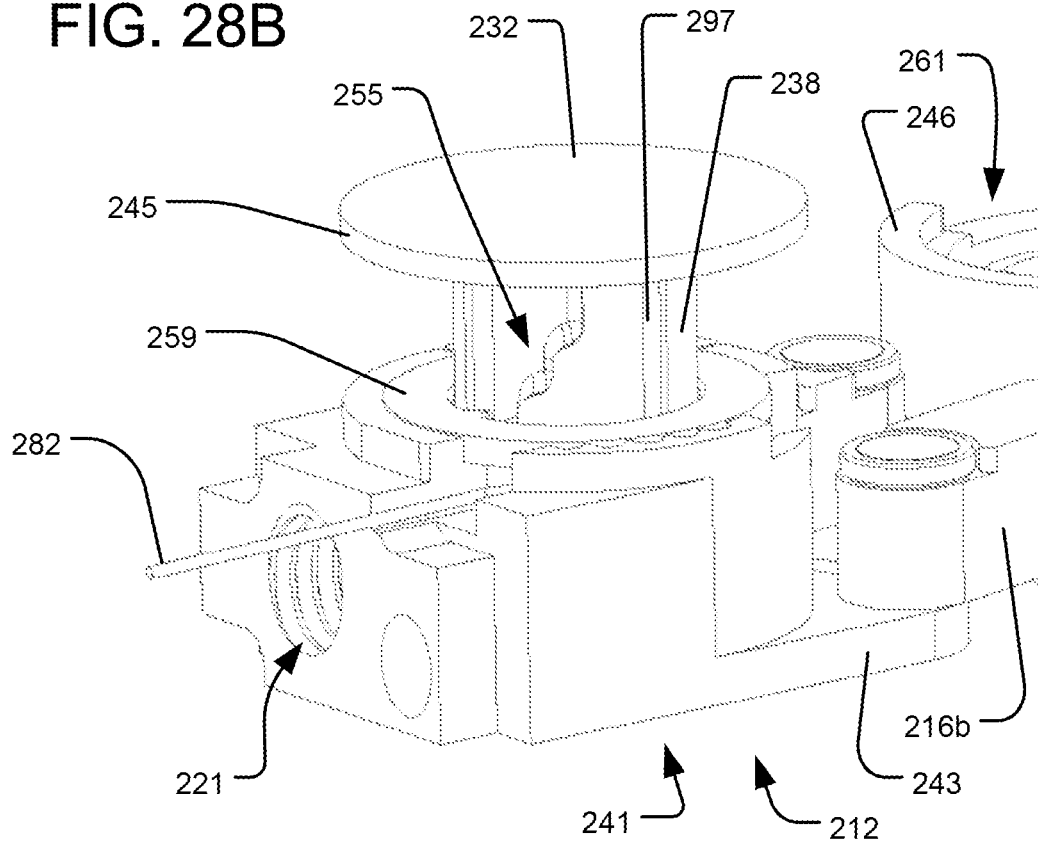
FIG. 28B is a partial perspective view of the spinal implant of FIG. 17 in a longitudinally expanded configuration.

The three segments 212, 214, 215 of the implant 210 may be interconnected by pivotable linkages 216 like those in implant 110, except that those illustrated in the embodiment of FIGS. 17-29 are all straight linkages 216. Having three (or more) interconnected, articulating segments 212, 214, 215 may thus allow for the insertion of the implant 210 in the manner shown in FIG. 18, after which the implant 210 can be articulated into an arrangement like that illustrated in FIG. 19. That is, the segments 212, 214, 215 may initially be oriented during insertion in an almost linear arrangement (as illustrated in FIG. 18), after which the segments may be articulated within the intervertebral space to create a more triangular arrangement of pistons (as illustrated in FIG. 19), with the entire implant 210 being disposed towards the anterior portion of the spine. The bottom plates 243 of each segment 212, 214, 215 may be shaped with notches 206 configured to receive portions of the bottom plates 243 of adjacent segments, as shown in FIG. 20, in order to facilitate the articulation of the segments into the triangular arrangement shown in FIG. 19. The implant 210 may then be expanded in the longitudinal direction of the spine (e.g., hydraulically) from the contracted configuration illustrated in FIG. 21A to the expanded configuration illustrated in FIG. 21B. As shown in FIG. 22B, any or all of the linkages 216 may be configured in the same manner as the linkages 116 of the embodiment of FIGS. 13-16, such that the linkages 216 can communicate the hydraulic fluid among all of the segments 212, 214, 215 via a series of channels 207 formed in the bottom plates 243.

In the embodiments of FIGS. 13-16 and 17-29, one or more pistons 238 may be independently controlled via a separate pressure channel. The different linkages 116, 216 may thus be on different pressure channel circuits that bypass certain pistons. As an example, in an embodiment having three segments such as that shown in FIGS. 17-29, the pressure channel communicating with the inner linkages 216a may bypass the piston 238 of the central segment 215, while communicating with the pistons 238 of the other segments 212, 214, and the pressure channel communicating with the outer linkages 216b may only serve the piston 238 of the central segment 215, while bypassing the pistons 238 of the other segments. Other embodiments may include any other combinations of pistons on different pressure channels.

The embodiment of FIGS. 17-29 may include a different locking system to lock the positions of the pistons 238 than those discussed above. That is, as shown in FIGS. 23-29, the locking system of each segment 212, 214, 215 of the implant 210 may include a lower lock support 251 coupled with the bottom plate 243, which lower lock support is movably engageable with an associated upper lock support 253 coupled to the expanding top plate 245. Like the upper lock supports 53a-c of the embodiment of FIGS. 10-11, the upper lock supports 253 of the embodiment of FIGS. 17-29 are integrally formed inside the respective pistons 238 and resemble an inverted spiral staircase. The lower lock supports 251 may also resemble an upright spiral staircase positioned within the respective cylinders 246. Unlike the embodiment of FIGS. 10-11, however, the lower lock supports 251 of the embodiment of FIGS. 17-29 are integrally formed within the respective cylinders 246. The upper and lower lock supports may thus be movably engageable with one another via rotation of the pistons 238 during expansion. Specifically, the outer surface of each piston 238 may include a cam profile 255 shaped for engagement with a cam follower pin 257 of a cam ring 259 that surrounds the piston 238 and is secured to cylinder 246. As shown in FIGS. 25A, 26, and 27A-B, the top end of the cylinder 246 may include a recess 261 shaped to receive the cam ring 259, and a projection 273 of the cam ring 259 may be shaped to be received within a corresponding relief 275 of the cylinder 246, so as to lock the rotational orientation of the cam ring 259. The engagement of the cam follower pin 257 and the cam profile 255 is such that, as one of the steps of the upper lock support 253 is displaced vertically above a corresponding step of the lower lock support 251 during expansion of the piston 238, the cam ring 259 causes the piston 238 to rotate (counterclockwise in the view shown in FIGS. 27-28) so that the step of the upper lock support 253 is moved into engagement with the next step up along the lower lock support 251. That action then continues for each successive step of the upper and lower lock support during the upward expansion of the piston 238. The vertical displacement of the piston 238 thus becomes locked at each successive step, since retraction of the piston 238 will cause the aligned steps of the upper and lower lock supports to engage, thereby preventing further downward movement of the piston 238.

The piston 238 may be controlled during expansion so that it is only permitted to rotate in a single direction, such as by a ratcheting mechanism. That way, when the expansion force is released from the piston 238, the piston will not be permitted to undo its rotation so as to retract more than the height of a single step of the upper and lower lock supports. The ratcheting mechanism may include a ratcheting ring 295 surrounding the piston 238 and fixed rotationally with respect to the piston 238. Specifically, the ratcheting ring 295 may include one or more keys 296 receivable within associated key slots 297 on the piston 238, so that the ratcheting ring 295 can maintain its vertical position with respect to the cylinder 246 while the ratcheting ring 295 rotates with the piston 238 as the piston expands upwardly. During that rotation, a ratcheting pawl 298 along the perimeter of the ratcheting ring 295 engages ratcheting teeth 299 formed along the cylinder 246. In the embodiment illustrated in FIGS. 27-28, the ratcheting ring 295 permits counterclockwise rotation of the piston 238 while resisting clockwise rotation of the piston 238. As shown in FIGS. 24, 25A 26, and 29C, the ratcheting ring 295 is received within an arcuate groove 205 at the top end of the cylinder 246, in order to constrain the position of the ratcheting ring about the longitudinal axis of the piston 238 while permitting the ratcheting ring to rotate about that axis, and the vertical position of the ratcheting ring 295 is constrained between the cam ring 259 and the top of the cylinder 246.

Figure 29A:
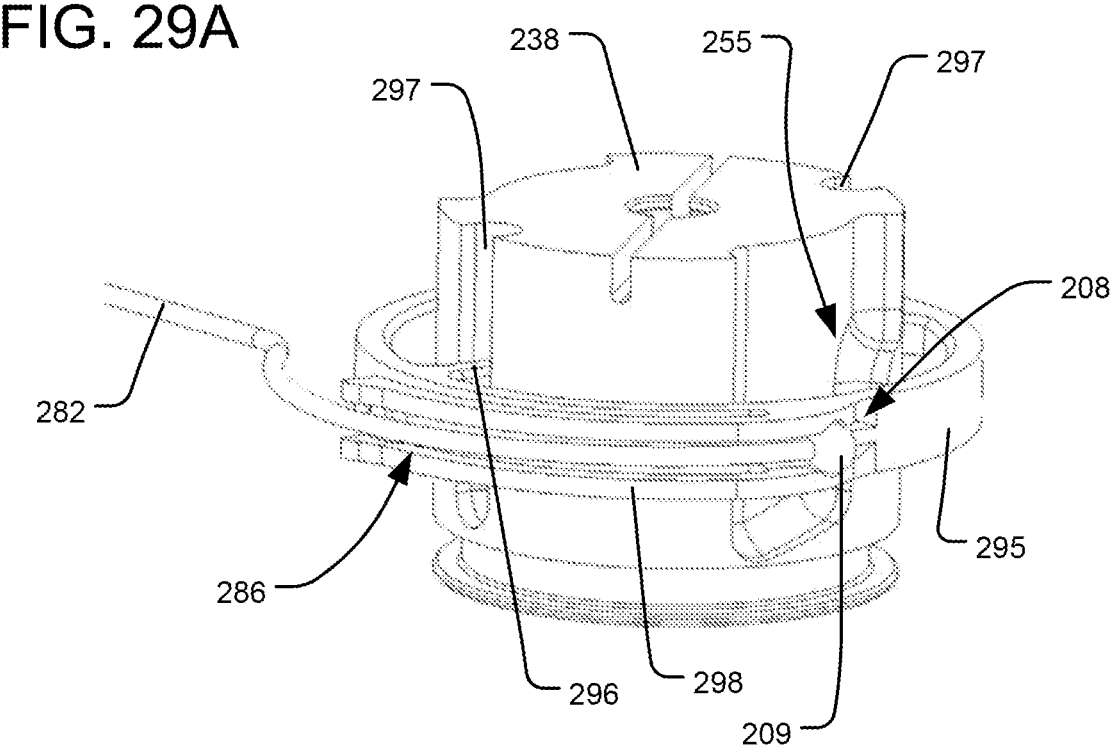
FIG. 29A is a perspective view of a subassembly of the spinal implant of FIG. 17, showing the piston, ratcheting ring, and control cable.
Figure 29B:
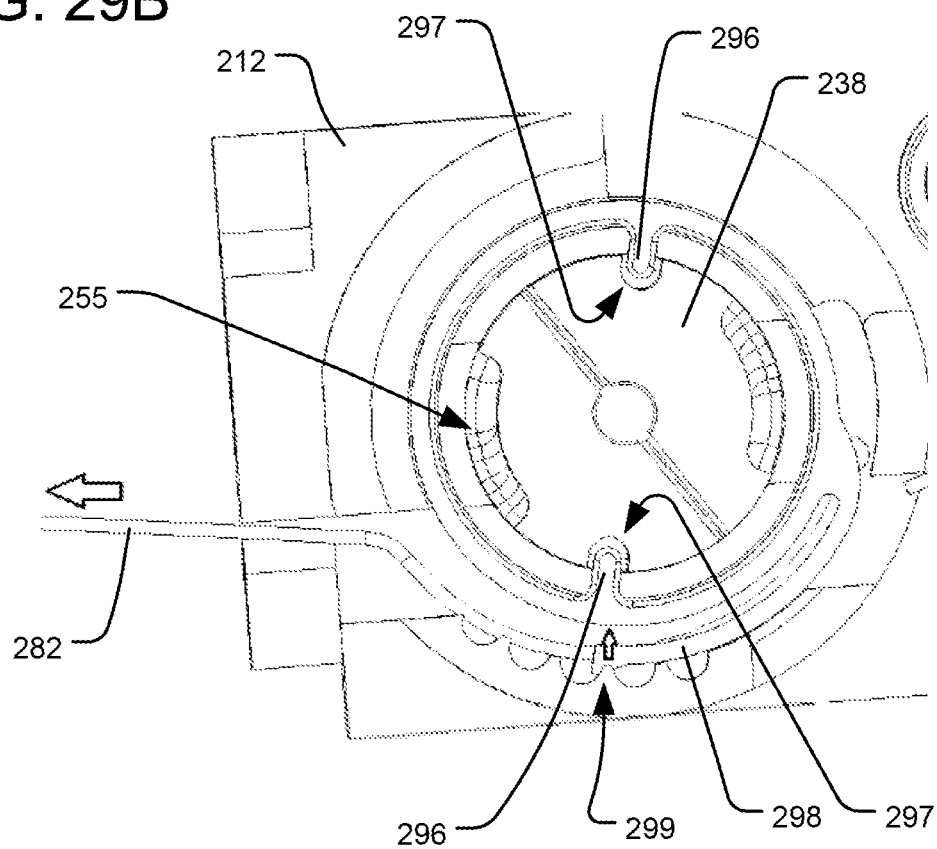
FIG. 29B is a partial top plan view of the spinal implant of FIG. 17 with the top plate 245 omitted.
Figure 29C:
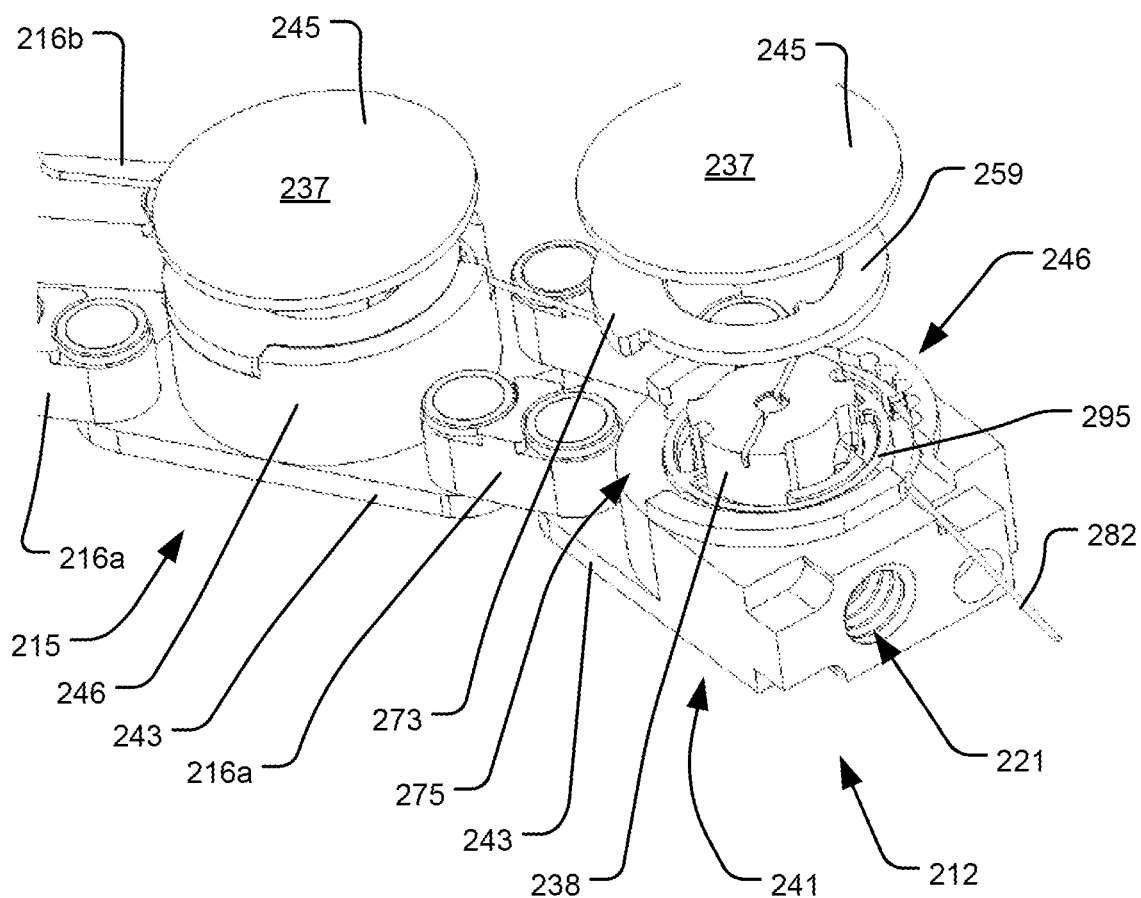
FIG. 29C is a partial, exploded perspective view of the spinal implant of FIG. 17.

If retraction of the pistons 238 is desired by the user, the ratcheting ring 295 can be unlocked so as to permit the rotation of the pistons to be reversed. Specifically, as shown in FIGS. 29A-C, a control cable 282 is received within a groove 286 in the ratcheting pawl 298, and the distal end of the control cable 282 may be fixed to the ratcheting ring 295 by an enlarged ball 209 received within a corresponding recess 208. By pulling proximally on the control cable 282, the ratcheting pawl 298 will deflect out of engagement with the ratcheting teeth 299 of the cylinder 246, as shown in FIG. 29B, thus permitting reverse rotation of the piston 238. Preferably, the ratcheting ring 295 of each segment 212, 214, 215 of the implant 210 includes its own respective control cable 282 extending proximally from the implant 210 for operation by the user. That way, the pistons 238 can be individually retracted, if desired. Alternatively, all of the ratcheting rings 295 may be interconnected for simultaneous unlocking, such as by having each of the ratcheting rings 295 connected to a single control cable, or by utilizing a series of control cables interconnecting the ratcheting rings 295 of each segment 212, 214, 215.

In order to avoid imparting the rotation of the pistons 238 to the vertebral bodies via the outwardly expanding top plates 245 that define the upper vertebral engaging surfaces 237, the top plates 245 may be connected to the respective pistons 238 by connections which permit rotation between those two components. For example, the top plates 245 may be connected to the associated pistons 238 via ball joints 204. Beneficially, such ball joint connections may also permit the top plates 245 to be angled with respect to the pistons 238 as needed, based on any angle defined between the vertebral body engaged by the top plates 245 (e.g., the vertebral body $V_s$ in the superior direction) and the bottom plates 243 defining the lower vertebral engaging surfaces 241.

Although not illustrated herein, the embodiment of the locking system shown in FIGS. 23-29 may be used in place of any of the other locking systems of the other embodiments disclosed in the present application. Moreover, pivotable connections (such as the ball joint 204 connections discussed above in connection with the embodiment of FIGS. 17-29) may be incorporated between the top plates and their associated pistons in any of the other embodiments of the present application.

Although it is possible to do so in an embodiment having two expandable segments (like that illustrated in FIGS. 13-16), is may be more desirable in an embodiment having three or more segments (like that illustrated in FIGS. 17-29) to have differently sized pistons interconnected by a common pressure channel, such that differential expanding forces can be applied, as discussed above in connection with the embodiment of FIGS. 1-9. For example, in the implant 210 of FIGS. 17-29, the central segment 215 may beneficially have a piston sized differently from the other two segments 212, 214 (which may have the same sizes as one another) in order to correct lordosis by applying a different (e.g., greater) amount of expansion at the anterior portion of the spine when the implant 210 is arranged in the manner illustrated in FIG. 19.

Any of the embodiments disclosed above may be used in any type of approach to the intervertebral space (e.g., PLIF, TLIF, and lateral), although certain approaches may be more preferred for certain implant configurations. For example, the embodiments of FIGS. 1-11 may be best suited for a PLIF approach, while the embodiments of FIGS. 13-29 may be best suited for a TLIF approach.

Although various sealing members (e.g., o-rings) have been disclosed above for maintaining seals between surfaces that move relative to one another, it is noted that alternative embodiments (not shown) need not include separate sealing members, and instead either or both of the movable components may be structured to be self sealing.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal implant for placement in an intervertebral space between a first vertebral body and a second vertebral body of a spine, the spinal implant comprising:
    a first portion having an upper vertebral engagement surface and an opposing lower vertebral engagement surface, the first portion having a first extendable support element including a first vertical post and a first pawl the first extendable support element being actuatable to move the upper and lower vertebral engagement surfaces of the first portion away from one another along a superior-inferior dimension;
    a second portion having an upper vertebral engagement surface and an opposing lower vertebral engagement surface, the second portion having a second extendable support element including a second vertical post, and a second pawl the second extendable support element being actuatable to move the upper and lower vertebral engagement surfaces of the second portion away from one another along the superior-inferior dimension
    a tool interface at a proximal end of the spinal implant configured to receivably couple a tool to the spinal implant; and
    a hinge connecting together the first and second portions such that the first and second portions are articulatable about the hinge;
    wherein the upper and lower vertebral engagement surfaces of the first portion are movable relative to one another along a superior-inferior dimension independently of movement of the upper and lower vertebral engagement surfaces of the second portion relative to one another along the superior-inferior dimension.

2. The spinal implant of claim 1, wherein the hinge includes a third extendable support element.

3. The spinal implant of claim 2, wherein the spinal implant is further configured such that when the first, second, and third extendable support elements expand, the first extendable support element applies a first expansion force, the second extendable element applies a second expansion force, and the third extendable element applies a third expansion force.

4. The spinal implant of claim 3, wherein the first, second, and third expansion forces are applied simultaneously.

5. The spinal implant of claim 3, wherein at least one of the first, second, or third expansion forces is greater than the other expansion forces.

6. The spinal implant of claim 1, wherein:
the tool includes a spreader for spreading apart the first and second portions of the spinal implant about the hinge, and
wherein the spreading apart of the first and second portions of the spinal implant about the hinge is independent of the relative movement of the upper and lower vertebral engagement surfaces of each of the first and second portions along the superior-inferior dimension.

7. The spinal implant of claim 1, further comprising a first control cable extending around an outer surface of the spinal implant and coupled to the first pawl and a second control cable extending around the outer surface of the spinal implant and coupled to the second pawl,
wherein each of the first and second control cables are coupleable to the tool such that pulling each of the first and second control cables by the tool causes the respective first and second pawls to disengage from the respective first and second vertical posts so as to allow the upper and lower vertebral engagement surfaces of the respective first and second portions to move towards one another along the superior-inferior dimension.

8. The spinal implant of claim 1, wherein the first extendable support element includes a first piston slidably received within a first cylinder and the second extendable support element includes a second piston slidably received within a second cylinder.

9. The spinal implant of claim 8, wherein the hinge includes a third piston slidably received within a third cylinder, each of the first, second, and third pistons are expandable by supplying hydraulic fluid through the tool to a port at the proximal end of the spinal implant.

10. The spinal implant of claim 9, wherein the spinal implant is configured to direct the hydraulic fluid from the port in the first portion to the second portion through the hinge.

11. The spinal implant of claim 8, wherein:
the first piston is connected to a first upper lock support configured to releasably engage a first lower lock support,
the second piston is connected to a second upper lock support configured to releasably engage a second lower lock support, and
the hinge includes a third extendable support element having a third piston slidably received within a third cylinder, the third piston connected to a third upper lock support configured to releasably engage a third lower lock support.

12. The spinal implant of claim 11, wherein each of the first, second, and third lower lock supports are rotationally biased into mating engagement of the respective first, second, and third upper lock supports such that the first, second, and third pistons are prevented from retracting back into its respective cylinder at one of a variety of heights when the respective upper and lower lock supports are engaged.

13. The spinal implant of claim 11, wherein the first, second, and third lower lock supports are configured to be unlocked by rotating the first, second, and third lower lock supports away from engagement with the respective first, second, and third upper lock supports such that the first, second, and third pistons can retract.

14. A method of expanding a spinal implant in an intervertebral space between a first vertebral body and a second vertebral body of a spine, the method comprising:
inserting the spinal implant with a tool located in a tool interface at a proximal end of the spinal implant configured to receivably couple the tool to the spinal implant into the intervertebral space;
spreading first and second articulatable portions of the implant apart with the tool about a hinge of the implant, wherein the first articulatable portion has a first extendable support element including a first vertical post and a first pawl the first extendable support element being actuatable to move an upper vertebral engagement surface and a lower vertebral engagement surface of the first portion away from one another, and wherein the second articulatable portion has a second extendable support element including a second vertical post, and a second pawl the second extendable support element being actuatable to move an upper vertebral engagement surface and a lower vertebral engagement surface of the second portion away from one another;
expanding the implant along a superior-inferior dimension by actuating the first and second extendable support elements.

15. The method of claim 14, wherein expanding the implant along a longitudinal axis of the spine is independent of the spreading of the first and second articulatable portions.

16. The method of claim 14, wherein when expanding the implant along a longitudinal axis of the spine the first extendable support element applies a first expansion force and the second extendable element applies a second expansion force.

17. The method of claim 16, wherein the first and second expansion forces are applied simultaneously.

18. The method of claim 16 wherein the first expansion force is greater than the second expansion force.

* * * * *